(12) United States Patent
Solá Parera et al.

(10) Patent No.: US 11,969,002 B2
(45) Date of Patent: Apr. 30, 2024

(54) SAVOURY AND MOUTHFULNESS TASTE ENHANCERS

(71) Applicant: LUCTA, S.A., Madrid (ES)

(72) Inventors: José Solá Parera, Mollet del Vallés (ES); Montserrat Argelagués Feu, La Garriga (ES); Thomas Hofmann, Neufahrn (DE); Oliver Frank, Allershausen (DE); Laura Brehm, Munich (DE)

(73) Assignee: LUCTA, S.A., Madrid (ES)

( * ) Notice: Subject to any disclaimer, the term of this patent is extended or adjusted under 35 U.S.C. 154(b) by 608 days.

(21) Appl. No.: 17/284,441

(22) PCT Filed: Oct. 9, 2019

(86) PCT No.: PCT/EP2019/077308
§ 371 (c)(1),
(2) Date: Apr. 9, 2021

(87) PCT Pub. No.: WO2020/074561
PCT Pub. Date: Apr. 16, 2020

(65) Prior Publication Data
US 2021/0337850 A1    Nov. 4, 2021

(30) Foreign Application Priority Data
Oct. 10, 2018  (EP) .................................. 18382718

(51) Int. Cl.
A23L 27/00       (2016.01)
A23K 20/137     (2016.01)
(Continued)

(52) U.S. Cl.
CPC ............ *A23L 27/88* (2016.08); *A23K 20/137* (2016.05); *A23L 27/2054* (2016.08);
(Continued)

(58) Field of Classification Search
CPC .. A23L 27/88; A23L 27/2054; A23L 27/2056; A23K 20/137; C07D 239/42;
(Continued)

(56) References Cited

U.S. PATENT DOCUMENTS

2006/0057268 A1   3/2006  Dewis et al.
2014/0127144 A1   5/2014  Yang et al.
2017/0332683 A1  11/2017  Frerot et al.

FOREIGN PATENT DOCUMENTS

EP    2496097 B1    3/2016

OTHER PUBLICATIONS

Jhoo et al., "Characterization of 2-methyl-4-amino-5-(2-methyl-3-furylthiomethyl)pyrimidine from Thermal Degradation of Thiamin", Journal of Agricultural and Food Chemistry. 50, 4055-4058. 2002. (Year: 2002).*

(Continued)

Primary Examiner — Nikki H. Dees
Assistant Examiner — Maura E. Sweeney
(74) Attorney, Agent, or Firm — Squire Patton Boggs (US) LLP

(57) ABSTRACT

The present invention relates to a compound of formula (I1); to a mixture comprising an amount from 86% to 99% by weight measured by quantitative proton-NMR of a compound of formula (IA), (IB), (IC), (ID), (IE), (IF), (IG), (IH) and (IJ); and an edible composition and an edible article comprising them. The invention also relates to processes for their preparation and their use as a savoury and mouthfulness taste enhancer; particularly kokumi and/or umami taste enhancer. Formulae (I') (IA), (IB), (IC), (ID), (IE), (IF), (IG), (IH), (IJ).

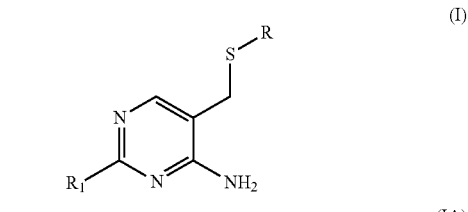

(I)

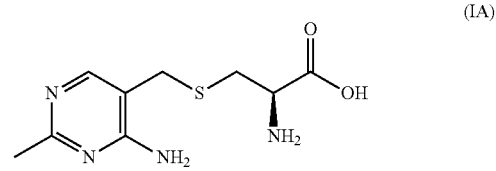

(IA)

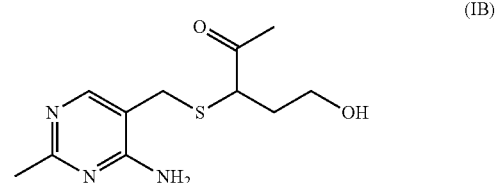

(IB)

(IC)

(ID)

(Continued)

-continued (IE)

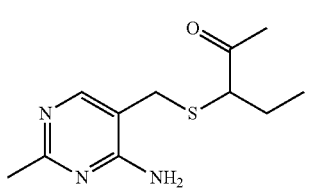

(IF)

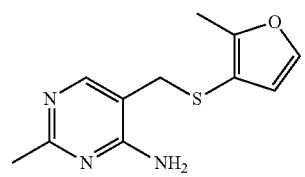

(IG)

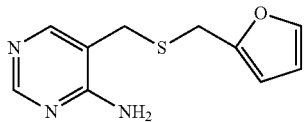

(IH)

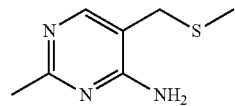

(IJ)

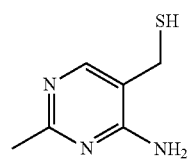

15 Claims, 8 Drawing Sheets

(51) Int. Cl.
*A23L 27/20* (2016.01)
*C07D 239/42* (2006.01)
*C07D 403/12* (2006.01)
*C07D 405/12* (2006.01)

(52) U.S. Cl.
CPC ........ *A23L 27/2056* (2016.08); *C07D 239/42* (2013.01); *C07D 403/12* (2013.01); *C07D 405/12* (2013.01); *A23V 2002/00* (2013.01)

(58) Field of Classification Search
CPC ... C07D 403/12; C07D 405/12; C07K 5/0606
See application file for complete search history.

(56) References Cited

OTHER PUBLICATIONS

Murata et al., "Vitamin B6 Antagonists and Growth of Lactic Acid Bacteria. I. Growth Inhibition by Pyrimidine Derivatives", The Journal of Vitaminology, 10, 237-242. 1964. (Year: 1964).*
International Search Report and Written Opinion dated Dec. 16, 2019 for International Application No. PCT/EP2019/077308, 16 pages.
Jhoo, et al: "Characterization of 2-Methyl-4-amino-5-(2-methyl-3-furylthiomethyl)pyrimidine from thermal degradation of thiamin," Journal of Agricultural and Food Chemistry; Jul. 1, 2002; vol. 50(14), pp. 4055-4058.
Okuda, et al: "Some analogs of Toxopyrimidine and Methioprim 1," Journal of Organic Chemisty; Nov. 1, 1958; vol. 23(11), pp. 1738-1741.
Lawless, et al: "Measurement of Sensory Thresholds," Sensory Evaluation of Food 2010, Springer $2^{nd}$ Edition; pp. 125-145.
ISO 10339; "International Standard: Sensory Analysis—Methodology—Duo-Trio Test;" Dec. 2017, 26 pages.

* cited by examiner

SAVOURY AND MOUTHFULNESS TASTE ENHANCERS

This application is a 35 U.S.C. § 371 application of PCT Application No. PCT/EP2019/077308, filed on Oct. 9, 2019, which claims priority to and the benefit of European Patent Application EP18382718.7 filed on Oct. 10, 2019; the entire contents of which are hereby incorporated by reference.

The present invention relates to the field of taste. Particularly, it relates to pyrimidine derived compounds having savoury and mouthfulness taste enhancing properties and its preparation processes. It also relates to edible compositions and edible articles containing them.

BACKGROUND ART

There is a constant need to discover new flavourings, i.e. taste-giving compounds or compounds that are able to impart, modify and/or enhance a taste impression. There is in particular a need for compounds which are able to impart (generate), modify and/or enhance the umami and/or kokumi taste impression. Consistent with the increasing health awareness of consumers, compounds are also sought which are able to impart, modify and/or enhance a salty taste. So, all in all, there is a particular need for savoury flavourings, which are able to impart, modify and/or enhance all the tastes umami, kokumi and salty.

Kokumi and umami are now established descriptors in the field of taste and are known to supplement, enhance, or modify the taste and/or aroma of a food without necessarily having a strong characteristic taste or aroma of their own. A desire for kokumi and umami exists for a wide range of foods like soups, sauces, savoury snacks, prepared meals, and condiments. Moreover, they are often found to complement or enhance foodstuffs which have a savoury or salty characteristic and, as a result, may be useful where sodium or salt reduction is desired.

"Kokumi" is a term used in the flavour industry to describe characteristics such as continuity, mouthfulness, richness and thickness. In contrast thereto, the sensory terms for the basic tastes are salty, sweet, sour, bitter or umami, the last-named being the taste of monosodium glutamate (MSG). Kokumi is a distinct taste quality, or rather a taste enhancing quality, which can be easily detected and differentiated by sensory tests by a trained panel. Compounds that provide a kokumi taste are usually tasteless in water, but enhance the taste in combination with other tastants in respect of the above mentioned qualities.

Umami or savoury taste is one of the five basic tastes together with sweetness, sourness, bitterness, and saltiness. The term umami was recognized as the scientific term to describe the taste of glutamates and nucleotides.

Umami represents the taste of the amino acid L-glutamate and 5'-ribonucleotides such as guanosine monophosphate (GMP) and inosine monophosphate (IMP). In particular, the sensation of umami is due to the detection of the carboxylate anion of glutamate in specialized receptor cells present on the human and other animal tongues. Its effect is to balance taste and round out the overall flavour of a dish. Umami enhances the palatability of a wide variety of foodstuffs. It has been described as a pleasant "brothy" or "meaty" taste with a long-lasting, mouth-watering and coating sensation over the tongue.

It has been disclosed in the state of the art compounds that impart and/or enhance the umami taste. In particular, glutamic acid imparts little umami taste, whereas the salts of glutamic acid, known as glutamates, give the characteristic umami taste due to their ionized state. In fact, monosodium glutamate (MSG) is an umami taste enhancer commonly added to Chinese food, canned vegetables, soups and processed meats.

However, individuals may exhibit allergic reactions such as burning sensation, headache, nausea, and chest pains when exposed to monosodium glutamate. Thus, people being sensitive to glutamate should avoid the use of it.

Several kokumi and/or umami taste enhancers have been disclosed in the state of the art. In particular, the United States patent application number US2006057268 discloses saturated or unsaturated N-alkamide as umami ingredients. Furthermore, the United States patent application number US20170332683 discloses amide derivatives of the cinnamic acid as umami taste of a flavouring composition or of a flavoured foodstuff.

On the other hand, The United States patent application US20140127144 discloses amide compounds derivatives.

However, there is still the need to provide efficient savoury and mouthfulness taste enhancers.

SUMMARY OF INVENTION

The inventors have found that pyrimidine derived compounds of formula (I'), having in the pyrimidine ring an alkyl moiety at position 2, an amine moiety at position 4 and a specific thiomethylene derived moiety at position 5 have the capacity of reinforcing (enhancing) the savoury and mouthfulness (i.e. kokumi and/or umami) taste of a flavoring composition or of an article (foodstuff) which comprises at least an savoury and mouthfulness imparting flavor compound.

In this regards, the inventors have found that pyrimidine derived compounds of formula (IA), (IB), (IC), (ID), (IE), (IF), (IG) and (IJ) having in the pyrimidine ring a methyl moiety at position 2, an amine moiety at position 4 and a specific thiomethylene derived moiety at position 5 of the present invention are appropriate for being used as savoury and mouthfulness (i.e. kokumi and/or umami) taste enhancing ingredients without imparting undesirable flavor notes.

Thus, a first aspect of the invention relates to a compound of formula (I')

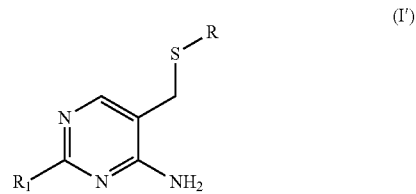

wherein:
R is a radical selected from the group consisting of

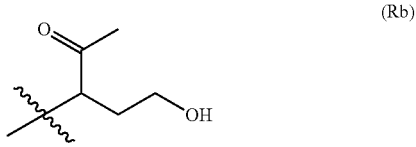

-continued

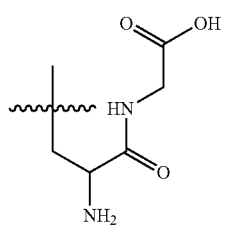
(Rc)

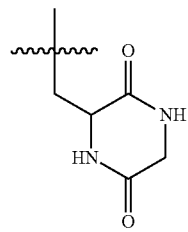
(Rd)

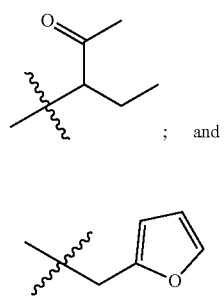
; and
(Re)

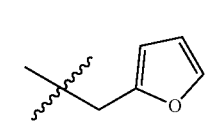
(Rg)

and $R_1$ is $(C_1-C_{12})$alkyl.

The second aspect of the invention relates to a mixture comprising an amount from 86% to 99% by weight measured by quantitative proton-NMR of:

(a) a compound of formula (I) selected from (IB), (IC), (ID), (IE) and (IG) as defined in the first aspect of the invention; or alternatively (b) a compound of formula (I) wherein R is

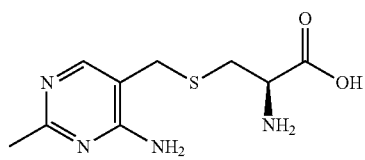
(Ra)

thereby the compound of formula (I) is

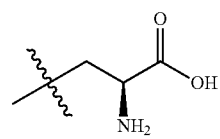
(IA)

or alternatively
(c) a compound of formula (I) wherein R is

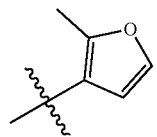
(Rf)

thereby the compound of formula (I) is

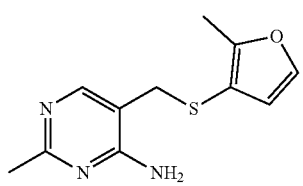
(IF)

or alternatively
(d) a compound of formula (I) wherein R is $CH_3$ (Rh) thereby the compound of formula (I) is

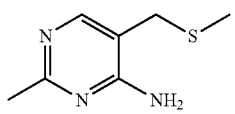
(IH)

or alternatively
(u) a compound of formula (I) wherein R is H (Rj) thereby the compound of formula (I) is

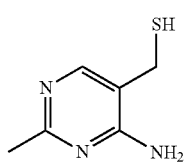
(IJ)

wherein:
when the mixture comprises the compound of formula (IA) or (IB), then the mixture is obtainable by a process which comprises reacting thiamine and L-cysteine followed by a preparative reversed-phase high-performance liquid chromatography purification; and isolating the corresponding fractions;
when the mixture comprises the compound of formula (IC) or (ID), then the mixture is obtainable by a process which comprises reacting thiamine and gluthation followed by a preparative reversed-phase high-performance liquid chromatography purification; and isolating the corresponding fractions;
when the mixture comprises the compound of formula (IE), then the mixture is obtainable by a process which comprises reacting 4-amino-5-(bromomethyl)-2-methylpyrimidin hydrobromide and 3-mercapto-2-pentanone followed by a preparative reversed-phase high-performance liquid chromatography purification;

when the mixture comprises the compound of formula (IF), then the mixture is obtainable by a process which comprises reacting thiamine and 2-methyl-3-furanthiol, followed by a preparative reversed-phase high-performance liquid chromatography purification; and isolating the corresponding fractions;

when the mixture comprises the compound of formula (IG), then the mixture is obtainable by a process which comprises reacting thiamine and 2-furanmethanethiol, followed by a preparative reversed-phase high-performance liquid chromatography purification; and isolating the corresponding fractions;

when the mixture comprises the compound of formula (IH), then the mixture is obtainable by a process which comprises reacting 4-amino-5-(bromomethyl)-2-methylpyrimidin Hydrobromide and sodium thiomethoxide, followed by a preparative reversed-phase high-performance liquid chromatography purification; and isolating the corresponding fractions; and when the mixture comprises the compound of formula (IJ), then the mixture is obtainable by a process which comprises reacting 4-amino-5-(bromomethyl)-2-methylpyrimidin and sodium thioacetate, adding sodium hydroxide and neutralizing with hydrochloric acid, followed by a preparative reversed-phase high-performance liquid chromatography purification; and isolating the corresponding fractions.

A third aspect of the invention relates to an edible composition comprising: one or more of the compounds of formula (IA), (IB), (IC), (ID), (IE), (IF), (IG), (IH), and (IJ); or alternatively one or more of the mixtures comprising an amount from 86% to 99% by weight measured by quantitative proton-NMR of a compound of formula (IA), (IB), (IC), (ID), (IE), (IF), (IG), (IH) and (IJ) as defined in the second aspect of the invention; one or more appropriate edible acceptable excipients or carriers; and optionally one or more savoury and mouthfulness imparting flavor compounds; particularly kokumi and/or umami imparting flavor compounds.

A fourth aspect of the invention relates to an edible article comprising: one or more of the compounds of formula (IA), (IB), (IC), (ID), (IE), (IF), (IG), (IH) and (IJ); or alternatively one or more of the mixtures comprising an amount from 86% to 99% by weight measured by quantitative proton-NMR of a compound of formula (IA), (IB), (IC), (ID), (IE), (IF), (IG), (IH) and (IJ) as defined in the second aspect of the invention; or alternatively the edible composition as defined in the third aspect of the invention; and a foodstuff base comprising one or more savoury and mouthfulness imparting flavor compounds; particularly kokumi.

Finally, a fifth aspect of the invention relates to the use of the compounds of formula (IA), (IB), (IC), (ID), (IE), (IF), (IG), (IH) and (IJ) as defined in the first aspect of the invention; or alternatively one or more of the mixtures comprising an amount from 86% to 99% by weight measured by quantitative proton-NMR of a compound of formula (IA), (IB), (IC), (ID), (IE), (IF), (IG), (IH) and (IJ) as defined in the second aspect of the invention; or alternatively an edible composition as defined in the third aspect of the invention as savoury and mouthfulness (i.e. kokumi and/or umami) taste enhancer.

DETAILED DESCRIPTION OF THE INVENTION

Figure 1A:
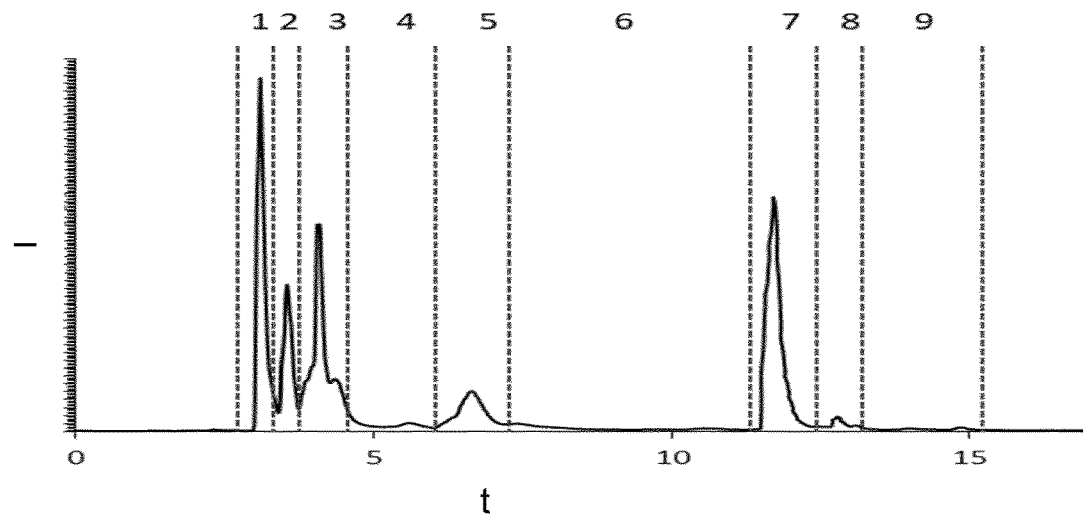
FIG. 1A refers to the nine fractions obtained by means of preparative RP-HPLC on a Phenyl-Hexyl column of the water fraction obtained in section 2.1.2. for the preparation of the mixture comprising an amount from 86% to 99% area/area measured by HPLC-MS of a compound of formula (IA). Units of the scheme are as follows: "I" is intensity in [mAU] and "t" is time in minutes.

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges given, such as temperatures, times, percentages of components and the like, should be considered approximate, unless specifically stated.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, tert-butyl, n-pentyl, and n-hexyl.

The term "halogen" refers to a fluoro, chloro, bromo or iodo.

The term "tosylate" refers to a substituent of the formula —OS(O)$_2$-4-methylphenyl (p-tolyl).

The term "mesylate" refers to a substituent of the formula —OS(O)$_2$ CH$_3$.

In the context of the invention, the term "molar ratio" refers to the number of moles of a component with respect to the number of moles of another component. For example, the number of moles of a first component of the NADES with respect to the number of moles of the second component of the NADES.

As mentioned above, the first aspect of the present invention refers to a compound of formula (I') as defined above.

In an embodiment, the compound of formula (I') is one of formula (I) wherein R1 is methyl and therefore the compound of the invention are compounds (IB), (IC), (ID), (IE) or (IG) as defined in the present invention In an embodiment, the compound of formula (I) is one wherein R is

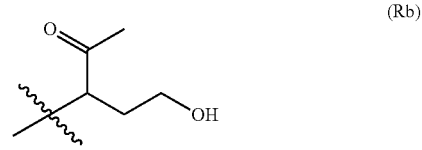 [SMILES: *C(CCO)C(C)=O]
(Rb)

and thereby it corresponds to the compound 3-(((4-amino-2-methyl-pyrimidin-5-yl)methyl)thio)-5-hydroxy-pentan-2-one of formula (IB)

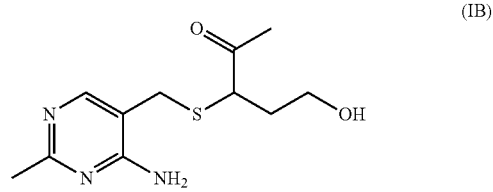 [SMILES: CC(=O)C(CCO)SCc1cnc(C)nc1N]
(IB)

In an embodiment, the compound of formula (I) is one wherein R is

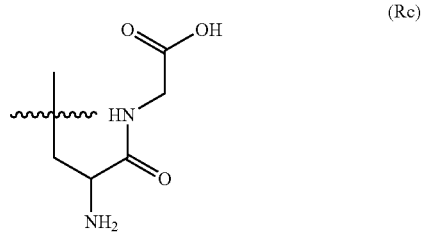 [SMILES: *CC(N)C(=O)NCC(=O)O]
(Rc)

and thereby it corresponds to the compound S-((4-amino-2-methylpyrimidin-5-yl)methyl)-cysteinylglycine of formula (IC)

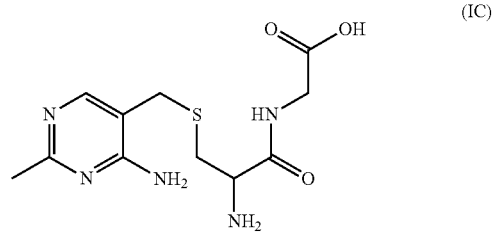 [SMILES: Cc1ncc(CSCC(N)C(=O)NCC(=O)O)c(N)n1]
(IC)

In an embodiment, the compound of formula (I) is one wherein R is

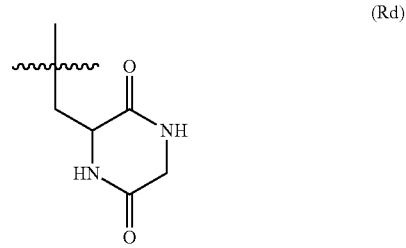 [SMILES: *CC1NC(=O)CNC1=O]
(Rd)

and thereby it corresponds to the compound 3-((((4-amino-2-methylpyrimidin-5-yl)methyl)thio)-methyl)piperazine-2,5-dione of formula

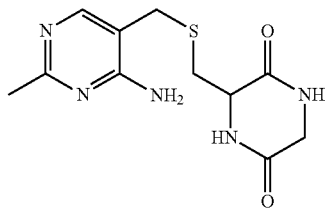
(ID)

In an embodiment, the compound of formula (I) is one wherein R is

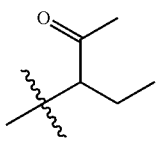
(Rd)

and thereby it corresponds to the compound 3-(((4-amino-2-methyl-pyrimidin-5-yl)methyl)thio)-pentan-2-one of formula (IE)

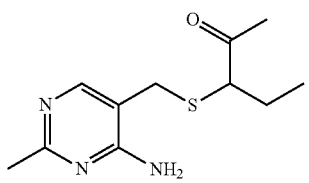
(IE)

In an embodiment, the compound of formula (I) is one wherein R is

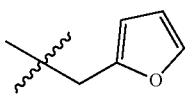 [SMILES: *Cc1ccco1]

and thereby it corresponds to the compound 5-(((furan-2-ylmethyl)thio)methyl)-2-methylpyrimidin-4-amine (IG)

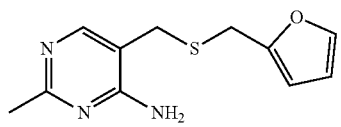
(IG)

In an embodiment, the compound of formula (IB), (IC), (ID), (IE) or (IG) is one having a chemical purity equal to or higher than 80% by weight measured by quantitative proton-NMR. In an embodiment, the compound of formula (IB), (IC), (ID), (IE) or (IG) is one having a chemical purity equal to or higher than 84% by weight measured by quantitative proton-NMR; particularly having a chemical purity equal to or higher than 86 area % measured by quantitative NMR.

In an embodiment, the compound of formula (IB), (IC), (ID), (IE) or (IG) is one having a chemical purity from 80% to 99% by weight measured by quantitative proton-NMR. In an embodiment, the compound of formula (IB), (IC), (ID), (IE) or (IG) is one having a chemical purity from 84% to 99% by weight measured by quantitative proton-NMR; particularly having a chemical purity from 86% to 99% by weight measured by quantitative proton-NMR.

As defined above, the second aspect of the present invention relates to a mixture comprising an amount from 86% to 99% by weight measured by quantitative proton-NMR of:
(a) a compound of formula (IB), (IC), (ID), (IE) or (IG); or alternatively
(b) a compound of formula (IA); or alternatively
(c) a compound of formula (IF); or alternatively
(d) a compound of formula (IH); or alternatively
(u) a compound of formula (IJ)
wherein:
when the mixture comprises the compound of formula (IA) or (IB), then the mixture is obtainable by a process which comprises reacting thiamine and L-cysteine followed by a preparative reversed-phase high-performance liquid chromatography purification; and isolating the corresponding fractions;
when the mixture comprises the compound of formula (IC) or (ID), then the mixture is obtainable by a process which comprises reacting thiamine and gluthation followed by a preparative reversed-phase high-performance liquid chromatography purification; and isolating the corresponding fractions;
when the mixture comprises the compound of formula (IE), then the mixture is obtainable by a process which comprises reacting 4-amino-5-(bromomethyl)-2-methylpyrimidin hydrobromide and 3-mercapto-2-pentanone followed by a preparative reversed-phase high-performance liquid chromatography purification;
when the mixture comprises the compound of formula (IF), then the mixture is obtainable by a process which comprises reacting thiamine and 2-methyl-3-furanthiol, followed by a preparative reversed-phase high-performance liquid chromatography purification; and isolating the corresponding fractions;
when the mixture comprises the compound of formula (IG), then the mixture is obtainable by a process which comprises reacting thiamine and 2-furanmethanethiol, followed by a preparative reversed-phase high-performance liquid chromatography purification; and isolating the corresponding fractions;
when the mixture comprises the compound of formula (IH), then the mixture is obtainable by a process which comprises reacting 4-amino-5-(bromomethyl)-2-methylpyrimidin Hydrobromide and sodium thiomethoxide, followed by a preparative reversed-phase high-performance liquid chromatography purification; and isolating the corresponding fractions; and
when the mixture comprises the compound of formula (IJ), then the mixture is obtainable by a process which comprises reacting 4-amino-5-(bromomethyl)-2-methylpyrimidin and sodium thioacetate, adding sodium hydroxide and neutralizing with hydrochloric acid, followed by a preparative reversed-phase high-performance liquid chromatography purification; and isolating the corresponding fractions.

For the purposes of the invention the expressions "obtainable", "obtained" and equivalent expressions are used interchangeably, and in any case, the expression "obtainable" encompasses the expression "obtained".

For the purposes of the invention, the compound of formula (I') which is a compound of formula (I) wherein R is

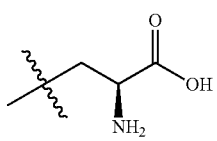

(Ra)

corresponds to the compound S-((4-amino-2-methylpyrimidin-5-yl)methyl)-L-cysteine of formula (IA)

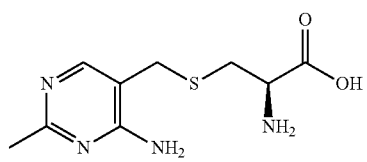

(IA)

In an embodiment, the mixture comprising an amount from 86% to 99% by weight measured by quantitative proton-NMR of a compound of formula (IA) is obtainable by a process which comprises: (a) heating a dissolution of a salt of thiamine and L-cysteine at a pH from 3 to 9 at a temperature from 60° C. to 200° C.; (b) extracting the reaction mixture obtained in step (a) with an organic solvent, to obtain a water fraction and an organic fraction; and (c) isolating the mixture comprising the compound of formula (IA) from the water fraction obtained in step (b) by means of the preparative reversed-phase high-performance liquid chromatography purification.

In an embodiment, the mixture comprising an amount from 86% to 99% by weight measured by quantitative proton-NMR of a compound of formula (IA) is obtainable by a process wherein in step (a) the salt of thiamine is selected from hydrochloride, mononitrate, and pyrophosphate; particularly the salt of thiamine is thiamine hydrochloride.

In an embodiment, the mixture comprising an amount from 86% to 99% by weight measured by quantitative proton-NMR of a compound of formula (IA) is obtainable by a process wherein step (a) is performed in the presence of a solvent. In an embodiment, the mixture comprising an amount from 86% to 99 by weight measured by quantitative proton-NMR of a compound of formula (IA) is obtainable by a process wherein step (a) is performed in the presence of a solvent selected from water, methanol, acetonitrile and dimethylformamide.

In an embodiment, the mixture comprising an amount from 86% to 99% by weight measured by quantitative proton-NMR of a compound of formula (IA) is obtainable by a process wherein step (a) is performed in the presence of a natural deep eutectic solvent (NADES).

As used herein, the term "Natural Deep Eutectic Solvents" and the abbreviation "NADES" have the same meaning and are used interchangeable. They refers to deep eutectic solvents and ionic liquids which are composed of two or more natural compounds that are present at high concentrations in all living cells and that form a eutectic system. In an embodiment, the NADES comprises two or more natural compounds. In an embodiment, the NADES comprises two or more natural compounds that include, but are not limited to adipic acid, alanine, arginine, asparagine, aspartic acid, citric acid, cysteine, fructose, galactose, glucose, glutamic acid, glutamine, inositol, isoleucine, lactic acid, lactose, leucine, lysine, malic acid, maltose, mannose, phenylalanine, proline, rhamnose, serine, succinic acid, sucrose, tartaric acid, threonine, tryptophan, valine, xylose, 1,2-propanediol, acetyl-glucosamine, aconitic acid, adonitol, benzoic acid, betaine, betaine hydrochloride, caffeic acid, carnitine, choline bitartrate, choline chloride, cinnamic acid, coumaric acid, cyclodextrin, deoxy-glucose, erythritol, ethylene glycol, gallic acid, glucosamine, glycerol, glycol, histidine, hydroxybenzoic acid, isomaltose, isosorbide, itaconic acid, levulinic acid, maleic acid, malonic acid, mandelic acid, mannitol, meso-erythritol, methionine, oxalic acid, phenylacetic acid, phenylpropionic acid, phytic acid sodium, proline, propanediol, ribitol, ribose, sodium hydroxide, sorbitol, sorbose, suberic acid, thiamine, thiamine hydrochloride, trehalose, tricarballylic acid, urea, vanillin, water or xylitol. In an embodiment, the NADES comprises two or more natural compounds selected from the group consisting of choline chloride, sucrose, water, glucose, sucrose, betaine, glycerol, proline, cysteine, malic, thiamine, thiamine hydrochloride, ribose and sodium hydroxide. In an embodiment, the NADES is selected from the group consisting of choline chloride/sucrose/water, glucose/sucrose/water, betaine/sucrose/water, betaine/glycerol/water, betaine/glucose/proline/water, cysteine/malic acid/water, thiamine hydrochloride/cysteine/ribose/water, thiamine hydrochloride/cysteine/ribose/sodium hydroxide/water, thiamine hydrochloride/proline/ribose/water and thiamine hydrochloride/proline/ribose/sodium hydroxide/water. In an embodiment, the NADES comprises two or more natural compounds selected from the group consisting of choline chloride, sucrose, water, glucose, sucrose, betaine, glycerol, proline, cysteine, malic, thiamine, thiamine hydrochloride, ribose and sodium hydroxide.

In an embodiment, the NADES is selected from the group consisting of choline chloride/sucrose/water, glucose/sucrose/water, betaine/sucrose/water, betaine/glycerol/water, betaine/glucose/proline/water, cysteine/malic acid/water, thiamine hydrochloride/cysteine/ribose/water, thiamine hydrochloride/cysteine/ribose/sodium hydroxide/water, thiamine hydrochloride/proline/ribose/water and thiamine hydrochloride/proline/ribose/sodium hydroxide/water.

In an embodiment, the NADES is one of the mixture of natural compounds disclosed in the Table below, wherein the amount of each natural compound is expressed in molar ratio:

| NADES number | Natural compounds | Molar ratio |
|---|---|---|
| NADES 1 | Choline chloride/sucrose/water | 4:1:4 |
| NADES 2 | glucose/sucrose/water | 1:1:9 |
| NADES 3 | betaine/sucrose/water | 2:1:9 |
| NADES 4 | betaine/glycerol/water | 1:2:2 |
| NADES 5 | betaine/glucose/proline/water | 1:1:1:4 |
| NADES 6 | cysteine/malic acid/water | 1:1:6 |
| NADES 7 | thiamine hydrochloride/cysteine/ribose/water | 1:1:2:6 |
| NADES 8 | thiamine hydrochloride/cysteine/ribose/sodium hydroxide/water | 1:1:2:1.5:6 |
| NADES 9 | thiamine hydrochloride/cysteine/ribose/sodium hydroxide/water | 1:1:2:3:6 |
| NADES 10 | thiamine hydrochloride/proline/ribose/water | 1:1:2:6 |

-continued

| NADES number | Natural compounds | Molar ratio |
| --- | --- | --- |
| NADES 11 | thiamine hydrochloride/proline/ribose/sodium hydroxide/water | 1:1:2:1.5:6 |
| NADES 12 | thiamine hydrochloride/proline/ribose/sodium hydroxide/water | 1:1:2:3:6 |

The process for the preparation of the above mentioned NADES comprises mixing all the components of the NADES at room temperature followed by heating the mixture thus obtained at a temperature from 20° C. to 150° C.; particularly from 50 to 80° C. until a viscous liquid mixture is obtained.

In an embodiment, the mixture comprising an amount from 86% to 99% by weight measured by quantitative proton-NMR of a compound of formula (IA) is obtainable by a process wherein step (a) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (IA) is obtainable by a process wherein step (a) is performed in the presence of a pH-regulating agent. In an embodiment, the mixture comprising an amount from 86% to 99 by weight measured by quantitative proton-NMR of a compound of formula (IA) is obtainable by a process wherein step (a) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (IA) is obtainable by a process wherein the temperature of step (a) is from 90° C. to 170° C.; from 110° C. to 130° C.; and particularly 120° C.

In an embodiment, the mixture comprising an amount from 86% to 99% by weight measured by quantitative proton-NMR of a compound of formula (IA) is obtainable by a process wherein in step (b) the organic solvent is selected from dichlormethane, hexane, diethylether, chloroform and ethyl acetate; particularly the solvent is ethyl acetate.

In an embodiment, the mixture comprising an amount from 86% to 99% by weight measured by quantitative proton-NMR of a compound of formula (IA) is obtainable by a process wherein step (c) comprises passing the water fraction through one or more reversed-phase columns under such chromatographic conditions that allows eluting the compound of formula (IA) and recovering a mixture comprising an amount from 86% to 99% by weight measured by quantitative proton-NMR of the compound of formula (IA).

In an embodiment, the mixture comprising an amount from 86% to 99% by weight measured by quantitative proton-NMR of a compound of formula (IA) is obtainable by a process wherein step (c) is performed by means of a preparative reversed-phase high-performance liquid chromatography sequence comprising: (c1) firstly, eluting the water fraction obtained in step (b) through a phenyl-Hexyl column using a gradient of 0.1% formic acid in water and acetonitrile; (c2) secondly, eluting through a Pentafluorphenyl column using a gradient of 0.1% formic acid in water and methanol; and (c3) thirdly, eluting through a TSKgel Amid-80 column using a gradient of 0.1% formic acid in water and acetonitrile.

In an embodiment, the mixture comprising an amount from 86% to 99% by weight measured by quantitative proton-NMR of a compound of formula (IA) is obtainable by a process wherein step (c) is performed by means of a preparative reversed-phase high-performance liquid chromatography sequence comprising: (c1) eluting the water fraction obtained in step (b) through a Phenyl-Hexyl column using a gradient of 0.1% formic acid in water and acetonitrile which comprises:

| time [min] | 0.1% formic acid in water: acetonitrile [%] |
| --- | --- |
| 0 | 100:0 |
| 5 | 100:0 |
| 10 | 60:40 |
| 12 | 0:100 |
| 14 | 0:100 |
| 17 | 100:0 |
| 20 | 100:0 | to obtain 9 fractions; (c2) eluting the second fraction obtained in step (c1) through a Pentafluorphenyl column using a gradient of 0.1% formic acid in water and methanol which comprises:

| time [min] | 0.1% formic acid in water: methanol [%] |
| --- | --- |
| 0 | 100:0 |
| 5 | 100:0 |
| 6 | 70:30 |
| 8 | 70:30 |
| 9 | 100:0 |
| 12 | 100:0 | to obtain 3 fractions; (c3) eluting the first fraction obtained in step (c2) through a TSKgel Amid-80 column using a gradient of 0.1% formic acid in water and acetonitrile which comprises:

| time [min] | 0.1% formic acid in water and acetonitrile [%] |
| --- | --- |
| 0 | 25:75 |
| 4 | 25:75 |
| 27 | 100:0 |
| 35 | 100:0 |
| 38 | 25:75 |
| 40 | 25:75 | to obtain 3 fractions; and (c4) isolating the third fraction obtained in step (c3) to obtain the mixture comprising an amount from 86% to 99% area/area measured by HPLC-MS of a compound of formula (IA).

In an embodiment, the mixture comprising an amount from 86% to 99% by weight measured by quantitative proton-NMR of a compound of formula (IA) is obtainable by a process which comprises performing the steps disclosed in Example 2.1 (cf. sections 2.1.1., 2.1.2. and 2.1.3.).

In an embodiment, the mixture comprising an amount from 86% to 99% by weight measured by quantitative proton-NMR of a compound of formula (IB) is obtainable by a process which comprises: (d) heating a dissolution of a salt of thiamine and L-cysteine at a pH of from 3 to 9 at a temperature from 60° C. to 200° C.; (e) extracting the reaction mixture obtained in step (d) with an organic solvent, to obtain a water fraction and an organic fraction; and (f) isolating the mixture comprising the compound of formula (IB) from the organic fraction obtained in step (e) by means of the preparative reversed-phase high-performance liquid chromatography purification.

In an embodiment, the mixture comprising an amount from 86% to 99% by weight measured by quantitative proton-NMR of a compound of formula (IB) is obtainable by a process wherein in step (d) the salt of thiamine is selected from hydrochloride, mononitrate, and pyrophosphate; particularly the salt of thiamine is thiamine hydrochloride.

In an embodiment, the mixture comprising an amount from 86% to 99% by weight measured by quantitative proton-NMR of a compound of formula (IB) is obtainable by a process wherein in step (d) is performed in the presence of a the solvent. In an embodiment, the mixture comprising an amount from 86% to 99 by weight measured by quantitative proton-NMR of a compound of formula (IA) is obtainable by a process wherein step (a) is performed in the presence of a solvent selected from water, methanol, acetonitrile and dimethylformamide.

In an embodiment, the mixture comprising an amount from 86% to 99% by weight measured by quantitative proton-NMR of a compound of formula (IB) is obtainable by a process wherein step (d) is performed in the presence of a natural deep eutectic solvent (NADES) as defined above in the present invention.

In an embodiment, the mixture comprising an amount from 86% to 99% by weight measured by quantitative proton-NMR of a compound of formula (IB) is obtainable by a process wherein step (d) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (IB) is obtainable by a process wherein step (d) is performed in the presence of a pH-regulating agent. In an embodiment, the mixture comprising an amount from 86% to 99 by weight measured by quantitative proton-NMR of a compound of formula (IB) is obtainable by a process wherein step (d) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (IB) is obtainable by a process wherein the temperature of step (d) is from 90° C. to 170° C.; from 110° C. to 130° C.; and particularly 120° C.

In an embodiment, the mixture comprising an amount from 86% to 99% by weight measured by quantitative proton-NMR of a compound of formula (IB) is obtainable by a process wherein in step (e) the organic solvent is selected from dichlormethane, hexane, diethylether, chloroform and ethyl acetate; particularly the solvent is ethylacetate.

In an embodiment, the mixture comprising an amount from 86% to 99% by weight measured by quantitative proton-NMR of a compound of formula (IB) is obtainable by a process wherein step (f) comprises passing the mixture to be purified through one or more reversed-phase columns under such chromatographic conditions that allows eluting the compound of formula (IB) and recovering a mixture comprising an amount from 86% to 99% by weight measured by quantitative proton-NMR of the compound of formula (IB).

In an embodiment, the mixture comprising an amount from 86% to 99% by weight measured by quantitative proton-NMR of a compound of formula (IB) is obtainable by a process wherein step (f) is performed by means of a preparative reversed-phase high-performance liquid chromatography sequence comprising: (f1) eluting the organic fraction obtained in step (e) through a MonoChrom column using a gradient of 0.1% formic acid in water and acetonitrile which comprises:

| time [min] | 0.1% formic acid in water: acetonitrile [%] |
| --- | --- |
| 0 | 100:0 |
| 2 | 100:0 |
| 14 | 60:40 |
| 15 | 0:100 |
| 16 | 0:100 |
| 17 | 100:0 |
| 20 | 100:0 | to obtain 5 fractions; (f2) eluting the fifth fraction obtained in step (f1) through a Pentafluorphenyl column using a gradient of 0.1% formic acid in water and methanol which comprises:

| time [min] | 0.1% formic acid in water:methanol [%] |
| --- | --- |
| 0 | 75:25 |
| 2 | 75:25 |
| 5 | 55:45 |
| 8 | 35:65 |
| 9 | 0:100 |
| 11 | 75:25 |
| 13 | 75:25 | to obtain 3 fractions; and (f3) isolating the third fraction obtained in step (f2) to obtain the mixture comprising an amount from 86% to 99% by weight measured by quantitative proton-NMR of a compound of formula (IB).

In an embodiment, the mixture comprising an amount from 86% to 99% by weight measured by quantitative proton-NMR of a compound of formula (IB) is obtainable by a process which comprises performing the steps disclosed in Example 2.1 (cf. sections 2.1.1., 2.1.2. and 2.1.4.).

In an embodiment, the mixture comprising an amount from 86% to 99% by weight measured by quantitative proton-NMR of a compound of formula (IC) is obtainable by a process which comprises: (g) heating a dissolution of a salt of thiamine and glutathione at a pH of from 3 to 9 at a temperature from 60° C. to 200° C.; and (h) isolating the mixture comprising the compound of formula (IC) from the reaction mixture obtained in step (g) by means of the preparative reversed-phase high-performance liquid chromatography purification.

In an embodiment, the mixture comprising an amount from 86% to 99% by weight measured by quantitative proton-NMR of a compound of formula (IC) is obtainable by a process wherein in step (g) the salt of thiamine is selected from hydrochloride, mononitrate, and pyrophosphate; particularly the salt of thiamine is hydrochloride thiamine.

In an embodiment, the mixture comprising an amount from 86% to 99% by weight measured by quantitative proton-NMR of a compound of formula (IC) is obtainable by a process wherein in step (g) is performed in the presence of a solvent. In an embodiment, the mixture comprising an amount from 86% to 99 by weight measured by quantitative proton-NMR of a compound of formula (IC) is obtainable by a process wherein step (g) is performed in the presence of a solvent selected from water, methanol, acetonitrile and dimethylformamide.

In an embodiment, the mixture comprising an amount from 86% to 99% by weight measured by quantitative proton-NMR of a compound of formula (IC) is obtainable by a process wherein step (g) is performed in the presence of a natural deep eutectic solvent (NADES) as defined above in the present invention.

In an embodiment, the mixture comprising an amount from 86% to 99% by weight measured by quantitative proton-NMR of a compound of formula (IC) is obtainable by a process wherein step (g) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (IC) is obtainable by a process wherein step (g) is performed in the presence of a pH-regulating agent. In an embodiment, the mixture comprising an amount from 86% to 99 by weight measured by quantitative proton-NMR of a compound of formula (IC) is obtainable by a process wherein step (d) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (IC) is obtainable by a process wherein the temperature of step (g) is from 90° C. to 170° C.; from 110° C. to 130° C.; and particularly 120° C.

In an embodiment, the mixture comprising an amount from 86% to 99% by weight measured by quantitative proton-NMR of a compound of formula (IC) is obtainable by a process wherein step (h) comprises passing the mixture to be purified through one or more reversed-phase columns under such chromatographic conditions that allows eluting the compound of formula (IC) and recovering a mixture comprising an amount from 86% to 99% by weight measured by quantitative proton-NMR of the compound of formula (IC).

In an embodiment, the mixture comprising an amount from 86% to 99% by weight measured by quantitative proton-NMR of a compound of formula (IC) is obtainable by a process wherein step (h) is performed by means of a preparative reversed-phase high-performance liquid chromatography sequence comprising: (h1) eluting the reaction mixture obtained in step (g) through a Phenyl-Hexyl column using a gradient of 0.1% formic acid in water and acetonitrile.

In an embodiment, the mixture comprising an amount from 86% to 99% by weight measured by quantitative proton-NMR of a compound of formula (IC) is obtainable by a process wherein step (h) is performed by means of a preparative reversed-phase high-performance liquid chromatography sequence comprising: (h1) eluting the reaction mixture obtained in step (g) through a Phenyl-Hexyl column using a gradient of 0.1% formic acid in water and acetonitrile which comprises:

| time [min] | 0.1% formic acid in water:acetonitrile [%] |
|---|---|
| 0 | 100:0 |
| 5 | 100:0 |
| 10 | 60:40 |
| 12 | 0:100 |
| 14 | 0:100 |
| 17 | 100:0 |
| 20 | 100:0 | to obtain 9 fractions; and (h2) isolating the third fraction obtained in step (h1) to obtain the mixture comprising an amount from 86% to 99% by weight measured by quantitative proton-NMR of a compound of formula (IC).

In an embodiment, the mixture comprising an amount from 86% to 99% by weight measured by quantitative proton-NMR of a compound of formula (IC) is obtainable by a process which comprises performing the steps disclosed in Example 2.2 (cf. sections 2.2.1. and 2.2.2.).

In an embodiment, the mixture comprising an amount from 86% to 99% by weight measured by quantitative proton-NMR of a compound of formula (ID) is obtainable by a process which comprises: (g) heating a dissolution of a salt of thiamine and glutathione at a pH of from 3 to 9 at a temperature from 60° C. to 200° C.; and (h) isolating the mixture comprising the compound of formula (ID) from the reaction mixture obtained in step (g) by means of the preparative reversed-phase high-performance liquid chromatography purification.

In an embodiment, the mixture comprising an amount from 86% to 99% by weight measured by quantitative proton-NMR of a compound of formula (ID) is obtainable by a process wherein in step (g) the salt of thiamine is selected from hydrochloride, mononitrate, and pyrophosphate; particularly the salt of thiamine is thiamine hydrochloride.

In an embodiment, the mixture comprising an amount from 86% to 99% by weight measured by quantitative proton-NMR of a compound of formula (ID) is obtainable by a process wherein in step (g) is performed in the presence of a solvent. In an embodiment, the mixture comprising an amount from 86% to 99 by weight measured by quantitative proton-NMR of a compound of formula (ID) is obtainable by a process wherein step (g) is performed in the presence of a solvent selected water, methanol, acetonitrile and dimethylformamide.

In an embodiment, the mixture comprising an amount from 86% to 99% by weight measured by quantitative proton-NMR of a compound of formula (ID) is obtainable by a process wherein step (g) is performed in the presence of a natural deep eutectic solvent (NADES) as defined above in the present invention.

In an embodiment, the mixture comprising an amount from 86% to 99% by weight measured by quantitative proton-NMR of a compound of formula (ID) is obtainable by a process wherein step (g) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (ID) is obtainable by a process wherein step (g) is performed in the presence of a pH-regulating agent. In an embodiment, the mixture comprising an amount from 86% to 99 by weight measured by quantitative proton-NMR of a compound of formula (ID) is obtainable by a process wherein step (g) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (ID) is obtainable by a process wherein the temperature of step (g) is from 90° C. to 170° C.; particularly from 110° C. to 130° C.; and particularly 120° C.

In an embodiment, the mixture comprising an amount from 86% to 99% by weight measured by quantitative proton-NMR of a compound of formula (ID) is obtainable by a process wherein step (h) comprises passing the mixture to be purified through one or more reversed-phase columns under such chromatographic conditions that allows eluting the compound of formula (ID) and recovering a mixture comprising an amount from 86% to 99% by weight measured by quantitative proton-NMR of the compound of formula (ID).

In an embodiment, the mixture comprising an amount from 86% to 99% by weight measured by quantitative proton-NMR of a compound of formula (ID) is obtainable by a process wherein step (h) is performed by means of a preparative reversed-phase high-performance liquid chromatography sequence comprising: (h1) eluting the reaction mixture obtained in step (g) through a Phenyl-Hexyl column using a gradient of 0.1% formic acid in water and acetonitrile.

In an embodiment, the mixture comprising an amount from 86% to 99% by weight measured by quantitative proton-NMR of a compound of formula (ID) is obtainable by a process wherein step (h) is performed by means of a preparative reversed-phase high-performance liquid chromatography sequence comprising: (h1) eluting the reaction mixture obtained in step (g) through a Phenyl-Hexyl column using a gradient of 0.1% formic acid in water and acetonitrile which comprises:

| time [min] | 0.1% formic acid in water:acetonitrile [%] |
| --- | --- |
| 0 | 100:0 |
| 5 | 100:0 |
| 10 | 60:40 |
| 12 | 0:100 |
| 14 | 0:100 |
| 17 | 100:0 |
| 20 | 100:0 | to obtain 9 fractions; and (h3) isolating the sixth fraction obtained in step (h1) to obtain the mixture comprising an amount from 86% to 99% by weight measured by quantitative proton-NMR of a compound of formula (ID).

In an embodiment, the mixture comprising an amount from 86% to 99% by weight measured by quantitative proton-NMR of a compound of formula (ID) is obtainable by a process which comprises performing the steps disclosed in Example 2.2 (cf. sections 2.2.1. and 2.2.2.).

In an embodiment, the mixture comprising an amount from 86% to 99% by weight measured by quantitative proton-NMR of a compound of formula (IE) is obtainable by a process which comprises: (i) heating a mixture of a compound of formula

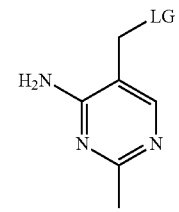

or a salt thereof and 3-mercapto-2-pentanone at a temperature from 0° C. to 60° C.; and (j) isolating the mixture comprising the compound of formula (IE) from the reaction mixture obtained in step (i) by means of the preparative reversed-phase high-performance liquid chromatography purification, wherein Lg is a leaving group selected from the group consisting of halogen, tosylate and mesylate.

In an embodiment, the mixture comprising an amount from 86% to 99% by weight measured by quantitative proton-NMR of a compound of formula (IE) is obtainable by a process wherein step (i) is performed heating a mixture of 4-amino-5-(halomethyl)-2-methylpyrimidin or a salt thereof; particularly 4-amino-5-(bromomethyl)-2-methylpyrimidin or a salt thereof.

In an embodiment, the mixture comprising an amount from 86% to 99% by weight measured by quantitative proton-NMR of a compound of formula (IE) is obtainable by a process wherein step (i) is performed heating a mixture of a salt of the compound of formula

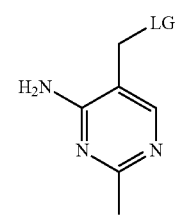

In an embodiment, the mixture comprising an amount from 86% to 99% by weight measured by quantitative proton-NMR of a compound of formula (IE) is obtainable by a process wherein step (i) is performed heating a mixture of a salt of the compound of formula

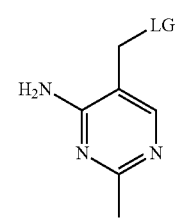

wherein the salt is selected from the group consisting of hybromide and dihydrobromide.

In an embodiment, the mixture comprising an amount from 86% to 99% by weight measured by quantitative proton-NMR of a compound of formula (IE) is obtainable by a process wherein step (i) is performed heating 4-amino-5-(halomethyl)-2-methylpyrimidin or a salt thereof; particularly 4-amino-5-(halomethyl)-2-methylpyrimidin hydrobromide.

In an embodiment, the mixture comprising an amount from 86% to 99% by weight measured by quantitative proton-NMR of a compound of formula (IE) is obtainable by a process wherein step (i) is performed using a compound 4-amino-5-(halomethyl)-2-methylpyrimidin Hydrobromide selected from the group consisting of 4-amino-5-(iodomethyl)-2-methylpyrimidin Hydrobromide, 4-amino-5-(bromomethyl)-2-methylpyrimidin Hydrobromide and 4-amino-5-(chloromethyl)-2-methylpyrimidin Hydrobromide.

In an embodiment, the mixture comprising an amount from 86% to 99% by weight measured by quantitative proton-NMR of a compound of formula (IE) is obtainable by a process wherein step (i) is performed in the presence of a solvent. In an embodiment, the mixture comprising an amount from 86% to 99 by weight measured by quantitative proton-NMR of a compound of formula (IE) is obtainable by a process wherein step (i) is performed in the presence of a solvent selected from tetrahydrofurane, pyridine, dimethylacetamide, triethylamide, dimethylamine and mixture thereof; particularly the solvent is dimethylformamide.

In an embodiment, the mixture comprising an amount from 86% to 99% by weight measured by quantitative proton-NMR of a compound of formula (IE) is obtainable by a process wherein step (i) is performed in the presence of a natural deep eutectic solvent (NADES) as defined above in the present invention.

In an embodiment, the mixture comprising an amount from 86% to 99% by weight measured by quantitative proton-NMR of a compound of formula (IE) is obtainable by a process wherein the temperature of step (i) is from 25° C. to 55° C.; particularly from 40° C. to 50° C.

In an embodiment, the mixture comprising an amount from 86% to 99% by weight measured by quantitative proton-NMR of a compound of formula (IE) is obtainable by a process wherein step (j) comprises passing the mixture to be purified through one or more reversed-phase columns under such chromatographic conditions that allows eluting the compound of formula (IE) and recovering a mixture comprising an amount from 86% to 99% area/area measured by HPLC-MS of the compound of formula (IE).

In an embodiment, the mixture comprising an amount from 86% to 99% by weight measured by quantitative proton-NMR of a compound of formula (IE) is obtainable by a process wherein step (j) is performed by means of a preparative reversed-phase high-performance liquid chromatography sequence comprising: (j1) eluting the reaction mixture obtained in step (i) through a Monochrom column using a gradient of 0.1% formic acid in water and acetonitrile.

In an embodiment, the mixture comprising an amount from 86% to 99% by weight measured by quantitative proton-NMR of a compound of formula (IE) is obtainable by a process wherein step (j) is performed by means of a preparative reversed-phase high-performance liquid chromatography sequence comprising: (j1) eluting the reaction mixture obtained in step (i) through a Monochrom column using a gradient of 0.1% formic acid in water and acetonitrile which comprises:

| time [min] | 0.1% formic acid in water:acetonitrile [%] |
|---|---|
| 0 | 100:0 |
| 2 | 100:0 |
| 14 | 60:40 |
| 15 | 0:100 |
| 16 | 0:100 |
| 17 | 100:0 |
| 20 | 100:0 | to obtain 6 fractions; and (j2) isolating the sixth fraction obtained in step (j1) to obtain the mixture comprising an amount from 86% to 99% by weight measured by quantitative proton-NMR of a compound of formula (IE).

In an embodiment, the mixture comprising an amount from 86% to 99% by weight measured by quantitative proton-NMR of a compound of formula (IE) is obtainable by a process which comprises performing the steps disclosed in Example 2.3 (cf. sections 2.3.1. and 2.3.2.).

For the purposes of the invention, the compound of formula (I') which is a compound of formula (I) wherein R is

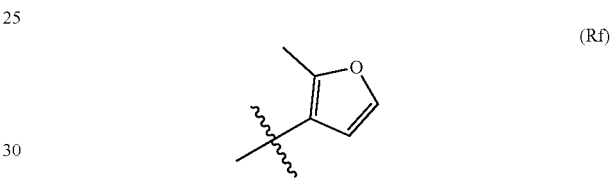

(Rf)

thereby the compound of formula (I) is

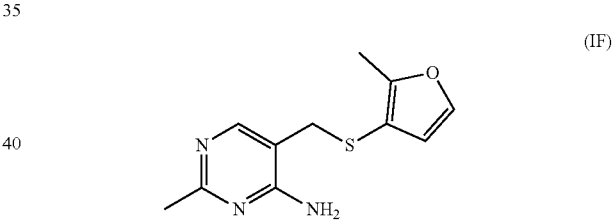

(IF)

In an embodiment, the mixture comprising an amount from 86% to 99% by weight measured by quantitative proton-NMR of a compound of formula (IF) is obtainable by a process which comprises: (k) heating a dissolution of a salt of thiamine and 2-Methyl-3-furanthiol at a pH of from 3 to 9 at a temperature from 60° C. to 200° C.; and (l) isolating the corresponding mixtures comprising the compound of formula (IF) from the reaction mixture obtained in step (k) by means of the preparative reversed-phase high-performance liquid chromatography purification.

In an embodiment, the mixture comprising an amount from 86% to 99% by weight measured by quantitative proton-NMR of a compound of formula (IF) is obtainable by a process wherein in step (k) the salt of thiamine is selected from hydrochloride, mononitrate, and pyrophosphate; particularly the salt of thiamine is thiamine hydrochloride.

In an embodiment, the mixture comprising an amount from 86% to 99% by weight measured by quantitative proton-NMR of a compound of formula (IF) is obtainable by a process wherein in step (k) is performed in the presence of a solvent. In an embodiment, the mixture comprising an amount from 86% to 99 area/area measured by HPLC-MS of a compound of formula (IF) is obtainable by a process wherein step (k) is performed in the presence of a solvent selected water, methanol, acetonitrile and dimethylformamide.

In an embodiment, the mixture comprising an amount from 86% to 99% by weight measured by quantitative proton-NMR of a compound of formula (IF) is obtainable by a process wherein step (k) is performed in the presence of a natural deep eutectic solvent (NADES) as defined above in the present invention.

In an embodiment, the mixture comprising an amount from 86% to 99% by weight measured by quantitative proton-NMR of a compound of formula (IF) is obtainable by a process wherein step (k) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (IF) is obtainable by a process wherein step (k) is performed in the presence of a pH-regulating agent. In an embodiment, the mixture comprising an amount from 86% to 99 area/area measured by HPLC-MS of a compound of formula (IF) is obtainable by a process wherein step (k) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (IF) is obtainable by a process wherein the temperature of step (k) is 10 from 90° C. to 170° C.; particularly from 110° C. to 130° C.; and particularly 120° C.

In an embodiment, the mixture comprising an amount from 86% to 99% by weight measured by quantitative proton-NMR of a compound of formula (IF) is obtainable by a process wherein step (I) is performed by means of a preparative reversed-phase high-performance liquid chromatography sequence comprising: (l1) firstly, eluting the reaction mixture obtained in step (k) through a MonoChrom column using a gradient of 0.1% formic 15 acid in water and acetonitrile; and (l2) secondly, eluting through a Pentafluorphenyl column using a gradient of 0.1% formic acid in water and acetonitrile.

In an embodiment, the mixture comprising an amount from 86% to 99% by weight measured by quantitative proton-NMR of a compound of formula (IF) is obtainable by a process wherein step (I) is performed by means of a preparative reversed-phase high-performance liquid chromatography sequence comprising: (l1) eluting the organic fraction obtained in step (k) through a MonoChrom column using a gradient of 0.1% formic acid in water and acetonitrile which comprises:

| time [min] | 0.1% formic acid in water:acetonitrile [%] |
| --- | --- |
| 0 | 100:0 |
| 2 | 100:0 |
| 14 | 60:40 |
| 15 | 0:100 |
| 16 | 0:100 |
| 17 | 100:0 |
| 20 | 100:0 | to obtain 5 fractions; (l2) eluting the fourth fraction obtained in step (l1) through a Pentafluorphenyl column using a gradient of 0.1% formic acid in water and acetonitrile which comprises:

| time [min] | 0.1% formic acid in water:acetonitrile [%] |
| --- | --- |
| 0 | 88:12 |
| 2 | 88:12 |
| 13 | 82:18 |
| 15 | 60:40 |
| 16 | 88:12 |
| 17 | 88:12 | to obtain 5 fractions; and (l3) isolating the fourth fraction obtained in step (l2) to obtain the mixture comprising an amount from 86% to 99% by weight measured by quantitative proton-NMR of a compound of formula (IF).

In an embodiment, the mixture comprising an amount from 86% to 99% by weight measured by quantitative proton-NMR of a compound of formula (IF) is obtainable by a process which comprises performing the steps disclosed in Example 2.4 (cf. sections 2.4.1. and 2.4.2.).

In an embodiment, the mixture comprising an amount from 86% to 99% by weight measured by quantitative proton-NMR of a compound of formula (IG) is obtainable by a process which comprises: (m) heating a dissolution of a salt of thiamine and 2-Furanmethanethiol at a pH of from 3 to 9 at a temperature from 60° C. to 200° C.; and (n) isolating the corresponding mixtures comprising the compound of formula (IG) from the reaction mixture obtained in step (m) by means of the preparative reversed-phase high-performance liquid chromatography purification.

In an embodiment, the mixture comprising an amount from 86% to 99% by weight measured by quantitative proton-NMR of a compound of formula (IG) is obtainable by a process wherein in step (m) the salt of thiamine is selected from hydrochloride, mono-nitrate, and pyrophosphate; particularly the salt of thiamine is thiamine hydrochloride.

In an embodiment, the mixture comprising an amount from 86% to 99% by weight measured by quantitative proton-NMR of a compound of formula (IG) is obtainable by a process wherein in step (m) is performed in the presence of a solvent. In an embodiment, the mixture comprising an amount from 86% to 99 by weight measured by quantitative proton-NMR of a compound of formula (IG) is obtainable by a process wherein step (m) is performed in the presence of a solvent selected water, methanol, acetonitrile and dimethylformamide.

In an embodiment, the mixture comprising an amount from 86% to 99% by weight measured by quantitative proton-NMR of a compound of formula (IG) is obtainable by a process wherein step (m) is performed in the presence of a natural deep eutectic solvent (NADES) as defined above in the present invention.

In an embodiment, the mixture comprising an amount from 86% to 99% by weight measured by quantitative proton-NMR of a compound of formula (IG) is obtainable by a process wherein step (m) is performed in the presence of a natural deep eutectic solvent (NADES) of betaine/glycerol/water, particularly at a molar ratio 1:2:2 (i.e. NADES 4).

In an embodiment, the mixture comprising an amount from 86% to 99% by weight measured by quantitative proton-NMR of a compound of formula (IG) is obtainable by a process wherein step (m) is performed in the presence of a pH-regulating agent. In an embodiment, the mixture comprising an amount from 86% to 99 by weight measured by quantitative proton-NMR of a compound of formula (IG) is obtainable by a process wherein step (m) is performed in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof.

In an embodiment, the mixture comprising an amount from 86% to 99% by weight measured by quantitative proton-NMR of a compound of formula (IG) is obtainable by a process wherein the temperature of step (m) is from 90° C. to 170° C.; particularly from 110° C. to 130° C.; and particularly 120° C.

In an embodiment, the mixture comprising an amount from 86% to 99% by weight measured by quantitative proton-NMR of a compound of formula (IG) is obtainable by a process wherein step (n) is performed by means of a preparative reversed-phase high-performance liquid chromatography sequence comprising: (n1) firstly, eluting the reaction mixture obtained in step (k) through a MonoChrom column using a gradient of 0.1% formic acid in water and acetonitrile; and (n2) secondly, eluting through a Pentafluorphenyl column using a gradient of 0.1% formic acid in water and acetonitrile.

In an embodiment, the mixture comprising an amount from 86% to 99% by weight measured by quantitative proton-NMR of a compound of formula (IG) is obtainable by a process wherein step (n) is performed by means of a preparative reversed-phase high-performance liquid chromatography sequence comprising: (n1) eluting the organic fraction obtained in step (m) through a MonoChrom column using a gradient of 0.1% formic acid in water and acetonitrile which comprises:

| time [min] | 0.1% formic acid in water: acetonitrile [%] |
| --- | --- |
| 0 | 100:0 |
| 2 | 100:0 |
| 14 | 60:40 |
| 15 | 0:100 |
| 16 | 0:100 |
| 17 | 100:0 |
| 20 | 100:0 | to obtain 5 fractions; (n2) eluting the fourth fraction obtained in step (n1) through a Pentafluorphenyl column using a gradient of 0.1% formic acid in water and acetonitrile which comprises:

| time [min] | 0.1% formic acid in water: acetonitrile [%] |
| --- | --- |
| 0 | 88:12 |
| 2 | 88:12 |
| 13 | 82:18 |
| 15 | 60:40 |
| 16 | 88:12 |
| 17 | 88:12 | to obtain 5 fractions; and (n3) isolating the fourth fraction obtained in step (n2) to obtain the mixture comprising an amount from 86% to 99% by weight measured by quantitative proton-NMR of a compound of formula (IG).

In an embodiment, the mixture comprising an amount from 86% to 99% by weight measured by quantitative proton-NMR of a compound of formula (IG) is obtainable by a process which comprises performing the steps disclosed in Example 2.5 (cf. sections 2.5.1. and 2.5.2.).

For the purposes of the invention, the compound of formula (I') which is a compound of formula (I) wherein R is $CH_3$ (Rh), thereby the compound of formula (I) is

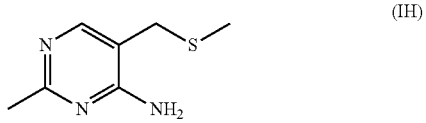

(IH)

In an embodiment, the mixture comprising an amount from 86% to 99% by weight measured by quantitative proton-NMR of a compound of formula (IH) is obtainable by a process which comprises: (p) heating a mixture of a salt of 4-amino-5-(bromomethyl)-2-methylpyrimidin and sodium thiomethoxide at a temperature from 25° C. to 55° C.; and (q) isolating the corresponding mixtures comprising the compound of formula (IH) from the reaction mixture obtained in step (p) by means of the preparative reversed-phase high-performance liquid chromatography purification.

In an embodiment, the mixture comprising an amount from 86% to 99% by weight measured by quantitative proton-NMR of a compound of formula (IH) is obtainable by a process wherein in step (p) is performed at a temperature of 40° C. to 60° C.; particularly 50° C.

In an embodiment, the mixture comprising an amount from 86% to 99% by weight measured by quantitative proton-NMR of a compound of formula (IH) is obtainable by a process wherein step (q) is performed by means of a preparative reversed-phase high-performance liquid chromatography sequence comprising: (q1) firstly, eluting the reaction mixture obtained in step (p) through a MonoChrom column using a gradient of 0.1% formic acid and acetonitrile; and (q2) secondly, eluting through a hydro RP using a gradient of 0.1% formic acid and acetonitrile.

In an embodiment, the mixture comprising an amount from 86% to 99% by weight measured by quantitative proton-NMR of a compound of formula (IH) is obtainable by a process wherein step (q) is performed by means of a preparative reversed-phase high-performance liquid chromatography sequence comprising: (q1) eluting the reaction mixture obtained in step (p) through a MonoChrom column using a gradient of 0.1% formic acid in water and acetonitrile which comprises:

| time [min] | 0.1% formic acid in water:acetonitrile [%] |
| --- | --- |
| 0 | 100:0 |
| 2 | 100:0 |
| 14 | 60:40 |
| 15 | 0:100 |
| 16 | 0:100 |
| 17 | 100:0 |
| 20 | 100:0 | to obtain four fractions; (q2) eluting the fourth fraction obtained in step (q1) through a hydro RP column using a isocratic elution 0.1% formic acid in water and acetonitrile in a proportion 92:8 to obtain two fractions; and (q3) isolating the second fraction obtained in step (q2) to obtain the mixture comprising an amount from 86% to 99% by weight measured by quantitative proton-NMR of a compound of formula (IH).

In an embodiment, the mixture comprising an amount from 86% to 99% by weight measured by quantitative proton-NMR of a compound of formula (IH) is obtainable by a process which comprises performing the steps disclosed in Example 2.7 (cf. sections 2.7.1. and 2.7.2.).

For the purposes of the invention, the compound of formula (I') which is a compound of formula (I) wherein R is H (Rj), thereby the compound of formula (I) is

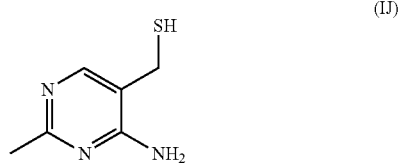

In an embodiment, the mixture comprising an amount from 86% to 99% by weight measured by quantitative proton-NMR of a compound of formula (IJ) is obtainable by a process which comprises: (r) heating a mixture of a salt of 4-amino-5-(bromomethyl)-2-methylpyrimidin and sodium thioacetate at a temperature from 25° C. to 55° C.; (s) heating the reaction mixture obtained in step (r) at a temperature from 25° C. to 55° C.; (t) adding sodium hydroxide and the resulting mixture is maintained at a temperature from 25° C. to 55° C.; (v) adding hydrochloric acid until neutralization; and (w) isolating the corresponding mixtures comprising the compound of formula (IJ) from the reaction mixture obtained in step (v) by means of the preparative reversed-phase high-performance liquid chromatography purification.

In an embodiment, the mixture comprising an amount from 86% to 99% by weight measured by quantitative proton-NMR of a compound of formula (IJ) is obtainable by a process wherein steps (r), (s), (t) and (v) are performed at a temperature of 40° C. to 60° C.; particularly 50° C.

In an embodiment, the mixture comprising an amount from 86% to 99% by weight measured by quantitative proton-NMR of a compound of formula (IJ) is obtainable by a process wherein step (w) is performed by means of a preparative reversed-phase high-performance liquid chromatography sequence comprising: (w1) eluting the reaction mixture obtained in step (v) through a MonoChrom column using a gradient of 0.1% formic acid in water and acetonitrile.

In an embodiment, the mixture comprising an amount from 86% to 99% by weight measured by quantitative proton-NMR of a compound of formula (IJ) is obtainable by a process wherein step (w) is performed by means of a preparative reversed-phase high-performance liquid chromatography sequence comprising: (w1) eluting the reaction mixture obtained in step (v) through a MonoChrom column using a gradient of 0.1% formic acid in water and acetonitrile which comprises:

| time [min] | 0.1% formic acid in water:acetonitrile [%] |
|---|---|
| 0 | 98:2 |
| 5 | 98:2 |
| 10 | 85:15 |

-continued

| time [min] | 0.1% formic acid in water:acetonitrile [%] |
|---|---|
| 11 | 60:40 |
| 12 | 98:2 |
| 17 | 98:2 | to obtain three fractions; (t2) isolating the third fraction obtained in step (w1) to obtain the mixture comprising an amount from 86% to 99% by weight measured by quantitative proton-NMR of a compound of formula (IJ).

In an embodiment, the mixture comprising an amount from 86% to 99% by weight measured by quantitative proton-NMR of a compound of formula (IJ) is obtainable by a process which comprises performing the steps disclosed in Example 2.8 (cf. sections 2.8.1. and 2.8.2.).

The compounds of formula (IB), (IC), (ID), (IE), or (IG) can be prepared according to the methods well known for a skilled person disclosed in the state of the art for the preparation of thioether compounds.

In an embodiment, the process for the preparation of compound of formula (IA) comprises reacting cysteine to the compound of formula

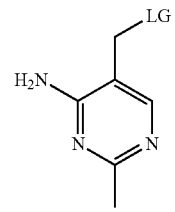

or a salt thereof as defined above. In an embodiment, the process for the preparation of compound of formula (IA) is performed in the presence of a solvent. In an embodiment, the process for the preparation of compound of formula (IA) is performed in the presence of a solvent selected from tetrahydrofurane, pyridine, dimethylacetamide, triethylamide, dimethylamine and mixture thereof; particularly the solvent is dimethylformamide. In an embodiment, the process for the preparation of compound of formula (IA) is performed at a temperature from 25° C. to 55° C.; particularly from 40° C. to 50° C.

In an alternative embodiment, the process for the preparation of compound of formula (IA) comprises reacting a mixture of a salt of thiamine and cysteine with thiaminase I. In an embodiment, the process for the preparation of compound of formula (IA) is performed with a salt of thiamine selected from the group consisting of hydrochloride, mononitrate, and pyrophosphate; particularly the salt of thiamine is thiamine hydrochloride. In an embodiment, the process for the preparation of compound of formula (IA) is performed in the presence of a pH-regulating agent; particularly, in the presence of pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IA) is performed at a temperature from 20° C. to 40° C.; particularly at room temperature. The term "room temperature" refers to a temperature at about 25 to 35° C. In an embodiment, the process for the preparation of compound of formula (IA) is performed in the presence of a solvent. In an embodiment, the process for the preparation of compound of formula (IA) is performed in the presence of a solvent selected from tetrahydrofurane, pyridine, dimethylacetamide, triethylamide, dimethylamine and mixture thereof; particularly the solvent is dimethylformamide.

In an embodiment, the process for the preparation of compound of formula (IB) comprises reacting cysteine to the compound of formula

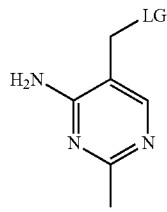

or a salt thereof as defined above. In an embodiment, the process for the preparation of compound of formula (IB) is performed in the presence of a solvent. In an embodiment, the process for the preparation of compound of formula (IB) is performed in the presence of a solvent selected from tetrahydrofurane, pyridine, dimethylacetamide, triethylamide, dimethylamine and mixture thereof; particularly the solvent is dimethylformamide. In an embodiment, the process for the preparation of compound of formula (IB) is performed at a temperature from 25° C. to 55° C.; particularly from 40° C. to 50° C.

In an alternative embodiment, the process for the preparation of compound of formula (IB) comprises reacting a mixture of a salt of thiamine and 3-mercapto-5-Hydroxy-2-pentanone with thiaminase I. In an embodiment, the process for the preparation of compound of formula (IB) is performed with a salt of thiamine selected from the group consisting of hydrochloride, mononitrate, and pyrophosphate; particularly the salt of thiamine is thiamine hydrochloride. In an embodiment, the process for the preparation of compound of formula (IB) is performed in the presence of a pH-regulating agent; particularly, in the presence of a pH regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IB) is performed at a temperature from 20° C. to 40° C.; particularly at room temperature. The term "room temperature" refers to a temperature at about 25 to 35° C. In an embodiment, the process for the preparation of compound of formula (IA) is performed in the presence of a solvent. In an embodiment, the process for the preparation of compound of formula (IB) is performed in the presence of a solvent selected from tetrahydrofurane, pyridine, dimethylacetamide, triethylamide, dimethylamine and mixture thereof; particularly the solvent is dimethylformamide.

In an embodiment, the process for the preparation of compound of formula (IC) comprises reacting cysteinylglycine to the compound of formula

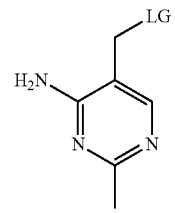

or a salt thereof as defined above. In an embodiment, the process for the preparation of compound of formula (IC) is performed in the presence of a solvent. In an embodiment, the process for the preparation of compound of formula (IC) is performed in the presence of a solvent selected from tetrahydrofurane, pyridine, dimethylacetamide, triethylamide, dimethylamine and mixture thereof; particularly the solvent is dimethylformamide. In an embodiment, the process for the preparation of compound of formula (IC) is performed at a temperature from 25° C. to 55° C.; particularly from 40° C. to 50° C.

In an embodiment, the process for the preparation of compound of formula (IB), (IE) or alternatively (IF) comprises heating thiamine. In an embodiment, the process for the preparation of compound of formula (IB), (IE) or alternatively (IF) comprises heating a dissolution of a salt of thiamine at a pH from 3 to 9 at a temperature from 60° C. to 200° C. In an embodiment, the process for the preparation of compound of formula (IB), (IE) or alternatively (IF) comprises heating a dissolution of a salt of thiamine at a pH from 3 to 9 at a temperature from 60° C. to 200° C.; particularly the salt of thiamine is selected from hydrochloride, mononitrate, and pyrophosphate; particularly the salt of thiamine is thiamine hydrochloride. In an embodiment, the process for the preparation of compound of formula (IB), (IE) or alternatively (IF) is performed in the presence of a solvent; particularly, in the presence of a solvent selected from water, methanol, acetonitrile and dimethylformamide. In an embodiment, the process for the preparation of compound of formula (IB), (IE) or alternatively (IF) is performed in the presence of a pH-regulating agent; particularly, in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IB), (IE) or alternatively (IF), particularly (IE), is performed at a temperature from 90° C. to 170° C.; from 110° C. to 130° C.; and particularly 120° C.

In an alternative embodiment, the process for the preparation of compound of formula (IG) comprises reacting a mixture of a salt of thiamine and 2-Furanmethanethiol with thiaminase I. In an embodiment, the process for the preparation of compound of formula (IG) is performed with a salt of thiamine selected from the group consisting of hydrochloride, mononitrate, and pyrophosphate; particularly the salt of thiamine is thiamine hydrochloride. In an embodiment, the process for the preparation of compound of formula (IG) is performed in the presence of a pH-regulating agent; particularly, in the presence of a ph-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IG) is performed at a temperature from 20° C. to 40° C.; particularly at room temperature. The term "room temperature" refers to a temperature at about 25 to 35° C. In an embodiment, the process for the preparation of compound of formula (IG) is performed in the presence of a solvent. In an embodiment, the process for the preparation of compound of formula (IG) is performed in the presence of a solvent selected from tetrahydrofurane, pyridine, dimethylacetamide, triethylamide, dimethylamine and mixture thereof; particularly the solvent is dimethylformamide.

In an alternative embodiment, the process for the preparation of compound of formula (IC) comprises reacting a mixture of a salt of thiamine and cysteinylglycine with thiaminase I. In an embodiment, the process for the preparation of compound of formula (IC) is performed with a salt of thiamine selected from the group consisting of hydrochloride, mononitrate, and pyrophosphate; particularly the salt of thiamine is thiamine hydrochloride. In an embodiment, the process for the preparation of compound of formula (IC) is performed in the presence of a pH-regulating agent; particularly, in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IC) is performed at a temperature from 20° C. to 40° C.; particularly at room temperature. The term "room temperature" refers to a temperature at about 25 to 35° C. In an embodiment, the process for the preparation of compound of formula (IC) is performed in the presence of a solvent. In an embodiment, the process for the preparation of compound of formula (IC) is performed in the presence of a solvent selected from tetrahydrofurane, pyridine, dimethylacetamide, triethylamide, dimethylamine and mixture thereof; particularly the solvent is dimethylformamide.

In an embodiment, the process for the preparation of compound of formula (ID) comprises reacting cyclo(L-cysteinylglycyl) to the compound of formula

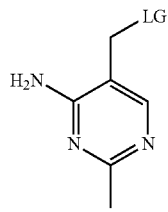

or a salt thereof as defined above. In an embodiment, the process for the preparation of compound of formula (ID) is performed in the presence of a solvent. In an embodiment, the process for the preparation of compound of formula (ID) is performed in the presence of a solvent selected from tetrahydrofurane, pyridine, dimethylacetamide, triethylamide, dimethylamine and mixture thereof; particularly the solvent is dimethylformamide. In an embodiment, the process for the preparation of compound of formula (ID) is performed at a temperature from 25° C. to 55° C.; particularly from 40° C. to 50° C.

In an alternative embodiment, the process for the preparation of compound of formula (ID) comprises reacting a mixture of a salt of thiamine and cyclo(L-cysteinylglycyl) with thiaminase I. In an embodiment, the process for the preparation of compound of formula (ID) is performed with a salt of thiamine selected from the group consisting of hydrochloride, mononitrate, and pyrophosphate; particularly the salt of thiamine is thiamine hydrochloride. In an embodiment, the process for the preparation of compound of formula (ID) is performed in the presence of a pH-regulating agent; particularly, in the presence of a ph-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (ID) is performed at a temperature from 20° C. to 40° C.; particularly at room temperature. The term "room temperature" refers to a temperature at about 25 to 35° C. In an embodiment, the process for the preparation of compound of formula (ID) is performed in the presence of a solvent. In an embodiment, the process for the preparation of compound of formula (ID) is performed in the presence of a solvent selected from tetrahydrofurane, pyridine, dimethylacetamide, triethylamide, dimethylamine and mixture thereof; particularly the solvent is dimethylformamide.

In an embodiment, the process for the preparation of compound of formula (IE) comprises heating thiamine with 3-Mercapto-2-pentanone. In an embodiment, the process for the preparation of compound of formula (IE) comprises heating a dissolution of a salt of thiamine and 3-Mercapto-2-pentanone at a pH from 3 to 9 at a temperature from 60° C. to 200° C. In an embodiment, the process for the preparation of compound of formula (IE) comprises heating a dissolution of a salt of thiamine and 3-Mercapto-2-pentanone at a pH from 3 to 9 at a temperature from 60° C. to 200° C.; particularly the salt of thiamine is selected from hydrochloride, mononitrate, and pyrophosphate; particularly the salt of thiamine is thiamine hydrochloride. In an embodiment, the process for the preparation of compound of formula (IE) is performed in the presence of a solvent; particularly, in the presence of a solvent selected from water, methanol, acetonitrile and dimethylformamide. In an embodiment, the process for the preparation of compound of formula (IE) is performed in the presence of a pH-regulating agent; particularly, in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IE) is performed at a temperature from 90° C. to 170° C.; from 110° C. to 130° C.; and particularly 120° C.

In an alternative embodiment, the process for the preparation of compound of formula (IE) comprises reacting a mixture of a salt of thiamine and 3-mercapto-2-pentanone with thiaminase I. In an embodiment, the process for the preparation of compound of formula (IE) is performed with a salt of thiamine selected from the group consisting of hydrochloride, mononitrate, and pyrophosphate; particularly the salt of thiamine is thiamine hydrochloride. In an embodiment, the process for the preparation of compound of formula (IE) is performed in the presence of a pH-regulating agent; particularly, in the presence of a ph-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IE) is performed at a temperature from 20° C. to 40° C.; particularly at room temperature. The term "room temperature" refers to a temperature at about 25 to 35° C. In an embodiment, the process for the preparation of compound of formula (IE) is performed in the presence of a solvent. In an embodiment, the process for the preparation of compound of formula (IE) is performed in the presence of a solvent selected from tetrahydrofurane, pyridine, dimethylacetamide, triethylamide, dimethylamine and mixture thereof; particularly the solvent is dimethylformamide.

In an embodiment, the process for the preparation of compound of formula (IG) comprises heating thiamine with 2-Furanmethanethiol. In an embodiment, the process for the preparation of compound of formula (IG) comprises heating a dissolution of a salt of thiamine and 2-Furanmethanethiol at a pH from 3 to 9 at a temperature from 60° C. to 200° C. In an embodiment, the process for the preparation of compound of formula (IG) comprises heating a dissolution of a salt of thiamine and 2-Furanmethanethiol at a pH from 3 to 9 at a temperature from 60° C. to 200° C.; particularly the salt of thiamine is selected from hydrochloride, mononitrate, and pyrophosphate; particularly the salt of thiamine is thiamine hydrochloride. In an embodiment, the process for the preparation of compound of formula (IG) is performed in the presence of a solvent; particularly, in the presence of a solvent selected from water, methanol, acetonitrile and dimethylformamide. In an embodiment, the process for the preparation of compound of formula (IG) is performed in the presence of a pH-regulating agent; particularly, in the presence of a pH-regulating agent selected from carbonic acid or an alkaline or alkaline earth salts thereof; citric acid or alkaline or alkaline earth salts thereof; ammonium buffers such as ammonium acetate, ammonium formate and ammonium dihydrogen phosphate and mixture thereof. In an embodiment, the process for the preparation of compound of formula (IG) is performed at a temperature from 90° C. to 170° C.; from 110° C. to 130° C.; and particularly 120° C.

In an embodiment, the process for the preparation of the compounds of formula (IB), (IC), (ID), (IE), or (IG) of the present invention comprises preparing the corresponding mixtures of the present invention as defined above which comprises an amount of a compound of formula (IB), (IC), (ID), (IE), or (IG) from 86% to 99% by weight measured by quantitative proton-NMR; followed by isolation of the compound of formula (IB), (IC), (ID), (IE) or (IG) from the mixture thus obtained.

All the embodiments disclosed above for the process for the preparation of the mixtures of the present invention as defined above which comprises an amount of a compound of formula (IB), (IC), (ID), (IE) or (IG) from 86% to 99% by weight measured by quantitative proton-NMR, also applies to the process for the preparation of the compounds of formula (IB), (IC), (ID), (IE) or (IG) of the present invention.

The isolation step of the compounds of formula (IB), (IC), (ID), (IE) or (IG) from the mixture of the invention comprising an amount of formula (IB), (IC), (ID), (IE) or (IG) form 86% to 99% by weight measured by quantitative proton-NMR can be performed according to the methods well known for a skilled person disclosed in the state of the art for the isolation of chemical compounds. In an embodiment, the isolation step may include removing them by one or more of the following operations: evaporation, lyophilisation, filtration, decantation and centrifugation, or other suitable techniques as known to a person skilled in the art; particularly under vacuum. Generally, the vacuum involves a pressure comprised from 0.5 mbar to 3 mbar.

In an embodiment, the isolation step of the compounds of formula (IB), (IC), (ID), (IE) or (IG) from the mixture of the invention further comprises submitting the isolated compound of formula (IB), (IC), (ID), (IE) or (IG) to a lyophilisation step. The conditions of the lyophilisation step are those known in the state of the art.

It is also a part of the invention a process for the preparation of the mixture of the invention comprising an amount of formula (IA), (IB), (IC), (ID), (IE) or (IG) from 86% to 99% by weight measured by quantitative proton-NMR.

The mixtures of the invention comprising an amount of formula (IA), (IB), (IC), (ID), (IE) or (IG) from 86% to 99% by weight measured by quantitative proton-NMR can be prepared according to the methods well known for a skilled person disclosed in the state of the art by the use of preparative reversed-phase high-performance liquid chromatography. The appropriate column, eluents and gradients can readily be determined by those skilled in the art according to the type of mixture being prepared.

In an embodiment, the process for the preparation of the mixture of the invention comprising an amount of formula (IA), (IB), (IC), (ID), (IE) or (IG) from 86% to 99% by weight measured by quantitative proton-NMR is the one disclosed above for the mixture characterized by its preparation process.

All embodiments disclosed above for the mixtures comprising an amount of a compound of formula (IA), (IB), (IC), (ID), (IE) or (IG) from 86% to 99% by weight measured by quantitative proton-NMR characterized by its preparation process also applies for the process of preparation of these mixtures.

As mentioned above, the third aspect of the invention relates to an edible composition comprising: one or more of the compounds of formula (IA), (IB), (IC), (ID), (IE), (IF), (IG), (IH) and (IJ); or alternatively one or more of the mixtures of the invention comprising an amount of formula (IA), (IB), (IC), (ID), (IE), (IF), (IG), (IH) and (IJ) from 86 to 99% by weight measured by quantitative proton-NMR; one or more appropriate edible acceptable excipients or carriers; and optionally one or more flavor compounds.

In an embodiment, the edible composition comprises: one or more of the compounds of formula (IA), (IB), (IC), (ID), (IE), (IF), (IG), (IH) and (IJ); one or more appropriate edible acceptable excipients or carriers; and optionally one or more flavor compounds.

In an embodiment, the edible composition comprises: one or more of the compounds of formula (IA), (IB), (IC), (ID), (IE), (IF), (IG), (IH) and (IJ); and one or more appropriate edible acceptable excipients or carriers.

In an embodiment, the edible composition comprises one or more flavor compounds. In an embodiment, the edible composition comprises one or more flavor compounds selected from the group consisting of savoury and mouthfulness imparting flavor compounds, sweet imparting compounds, and salty imparting compounds.

In an embodiment, the edible composition comprises one or more savoury and mouthfulness imparting flavor compounds; particularly kokumi and/or umami imparting flavor compounds.

The term "edible" refers to ingredients including one or more of the compounds of formula (IA), (IB), (IC), (ID), (IE), (IF), (IG), (IH) or (IJ) above and one or more of the mixtures of the invention comprising an amount of formula (IA), (IB), (IC), (ID), (IE), (IF), (IG), (IH) and (IJ) from 86% to 99% by weight measured by quantitative proton-NMR; compositions or articles that may be consumed by humans without significant deleterious health consequences.

The term "edible acceptable excipients or carriers" refers to excipients or carriers which are substantially neutral from a flavor point of view, insofar as it does not significantly alter the organoleptic properties of flavoring ingredients. Further, they are suitable for use in the preparation of compositions which can be consumed by humans without significant deleterious health consequences.

The edible compositions of the invention can be formulated in several forms that include, but are not limited to, solid or liquid forms. Additionally, the edible compositions of the present invention may contain other ingredients, such as colorants and light resistance agents, and other components known in the state of the art for use in edible compositions.

The edible compositions of the present invention can be prepared according to methods well known in the state of the art. The appropriate edible acceptable excipients and/or carriers, and their amounts, can readily be determined by those skilled in the art according to the type of compositions being prepared.

In an embodiment, the edible composition comprises one or more of the compounds of formula (IA), (IB), (IC), (ID), (IE), (IF), (IG), (IH) or (IJ); or alternatively one or more of the mixtures of the invention comprising an amount of formula (IA), (IB), (IC), (ID), (IE), (IF), (IG), (IH) or (IJ) from 86% to 99% by weight measured by quantitative proton-NMR; and one or more appropriate edible acceptable excipients or carriers. In an embodiment, the edible composition comprises one or more of the compounds of formula (IA), (IB), (IC), (ID), (IE), (IF), (IG), (IH) or (IJ); and one or more appropriate edible acceptable excipients or carriers.

In an embodiment, the edible composition comprises one or more of the compounds of formula (IA), (IB), (IC), (ID), (IE), (IF), (IG), (IH) or (IJ); or alternatively one or more of the mixtures of the invention comprising an amount of formula (IA), (IB), (IC), (ID), (IE), (IF), (IG), (IH) or (IJ) from 86% to 99% by weight measured by quantitative proton-NMR; one or more appropriate edible acceptable excipients or carriers; and one or more savoury and mouthfulness imparting flavor compounds; particularly kokumi and/or umami imparting flavor compounds. In an embodiment, the edible composition comprises one or more of the compounds of formula (IA), (IB), (IC), (ID), (IE), (IF), (IG), (IH) or (IJ); one or more appropriate edible acceptable excipients or carriers; and one or more savoury and mouthfulness imparting flavor compounds; particularly kokumi and/or umami imparting flavor compounds.

In an embodiment, the edible composition of the present invention comprises an amount of the compound of formula (IA), (IB), (IC), (ID), (IE), (IF), (IG), (IH) or (IJ) from 5 mg to 50 mg per Kg of the edible composition. In an embodiment, the edible composition of the present invention comprises an amount of the compound of formula (IA), (IB), (IC), (ID), (IE), (IF), (IG), (IH) or (IJ) from 86% to 99% by weight of the composition. All the embodiments disclosed for the compounds of formula (IA), (IB), (IC), (ID), (IE), (IF), (IG), (IH) or (IJ), or for the mixtures comprising a compound of formula (IA), (IB), (IC), (ID), (IE), (IF), (IG), (IH) or (IJ) from 86% to 99% by weight measured by quantitative proton-NMR also applies for the edible composition of the third aspect of the invention.

As mentioned above, the fourth aspect of the invention relates to an edible article comprising: one or more of the compounds of formula (IA), (IB), (IC), (ID), (IE), (IF), (IG), (IH) or (IJ); or alternatively one or more of the mixtures of the invention comprising a compound of formula (IA), (IB), (IC), (ID), (IE), (IF), (IG), (IH) or (IJ) from 86% to 99% by weight measured by quantitative proton-NMR; or alternatively the edible composition as defined in the third aspect of the invention; and a foodstuff base comprising one or more flavor compounds.

In an embodiment, the edible article comprises: one or more of the compounds of formula (IA), (IB), (IC), (ID), (IE), (IF), (IG), (IH) or (IJ); or alternatively the edible composition as defined in the third aspect of the invention; and a foodstuff base comprising one or more flavor compounds.

In an embodiment, the edible article comprises: one or more of the compounds of formula (IA), (IB), (IC), (ID), (IE), (IF), (IG), (IH) and (IJ); or alternatively the edible composition as defined in the third aspect of the invention and a foodstuff base comprising one or more flavor compounds selected from the group consisting of savoury and mouthfulness imparting flavor compounds, sweet imparting compounds, and salty imparting compounds.

In an embodiment, the edible article comprises: one or more of the compounds of formula (IA), (IB), (IC), (ID), (IE), (IF), (IG), (IH) and (IJ); or alternatively the edible composition as defined in the third aspect of the invention and a foodstuff base comprising one or more flavor compounds is a savoury and mouthfulness imparting flavor compounds.

In an embodiment, the edible article comprises: one or more of the compounds of formula (IA), (IB), (IC), (ID), (IE), (IF), (IG), (IH) and (IJ); or alternatively the edible composition as defined in the third aspect of the invention and a foodstuff base comprising one or more flavor compounds which are savoury and mouthfulness imparting flavor compounds; particularly kokumi and/or umami imparting flavor compounds.

In an embodiment, the edible article comprising: one or more of the compounds of formula (IA), (IB), (IC), (ID), (IE), (IF), (IG), (IH) or (IJ); or alternatively one or more of the mixtures of the invention comprising a compound of formula (IA), (IB), (IC), (ID), (IE), (IF), (IG), (IH) or (IJ) from 86% to 99% by weight measured by quantitative proton-NMR; or alternatively the edible composition as defined in the third aspect of the invention; and a foodstuff base comprising one or more savoury and mouthfulness imparting flavor compounds; particularly kokumi and/or umami imparting flavor compounds. In an embodiment, the edible article comprising: one or more of the compounds of formula (IA), (IB), (IC), (ID), (IE), (IF), (IG), (IH) or (IJ); or alternatively the edible composition as defined in the third aspect of the invention; and a foodstuff base comprising one or more savoury and mouthfulness imparting flavor compounds; particularly kokumi and/or umami imparting flavor compounds.

The term "flavor compounds" refers to any compound that has flavor properties. It means any compound that gives another substance flavor which affects the sense of taste of the compound, such as for example causing it to become sweet, savoury, mouthfulness, sour or salty.

The term "savoury and mouthfulness imparting flavor compounds" refers to any compound that has flavor properties and is capable of becoming another substance full of flavor, delicious and tasty. The term "umami imparting flavor compounds" refers to any compound that has umami flavor properties. Examples of appropriate umami imparting flavor compounds for the present invention include, but not limited to, glutamic acid and a salt thereof, aspartic acid and a salt thereof, succinic acid, inosine monophosphate, guanosine monophosphate, and mixture thereof.

The term "kokumi imparting flavor compounds" refers to any compound that has kokumi flavor properties.

Examples of appropriate kokumi imparting flavor compounds for the present invention include, but not limited to glutamic acid and a salt thereof, aspartic acid and a salt thereof, succinic acid, inosine monophosphate, guanosine monophosphate, glutathione, gamma glutamyl peptide and a mixture thereof.

The terms "sweet imparting compounds" or "sweetener" has the same meaning and are used interchangeable. They refers to any compound that has sweet flavor properties including without any limitation any natural or synthesized sweet flavor compound that elicits a perception of sweetness. Examples of appropriate sweet imparting compounds for the present invention include, but not limited to non-caloric sweetener, a reduced calorie sweetener, or a non-target caloric sweetener.

The term "salty imparting compounds" refers to any compound that has salty flavor properties including any limitation any natural or synthesized salty flavor compound that elicits a perception of saltness. Examples of appropriate salty flavor imparting compounds for the present invention include, but not limited to edible chloride salts of alkaline and alkaline earth metals such as for example sodium, potassium and magnesium; or arginyl peptides.

The term "foodstuff base" refers to an edible product for instance a human being food, an animal food (i.e. feed) or a beverage that has one or more savoury and mouthfulness imparting flavor compounds; particularly kokumi and/or umami imparting flavor compounds.

In an embodiment, the edible article is one wherein the foodstuff base is a human being food. In an embodiment, the edible article is one wherein the foodstuff base is an animal food (feed).

In an embodiment, the edible article is one wherein the foodstuff base which comprises one or more umami imparting flavor compounds is selected from the group consisting of seasonings, condiments, a meat-based product, a soup, a carbohydrate-based product, a dairy or fat product, a savory product, and a pet or animal food. Suitable foodstuff bases can be fried or not, frozen or not, low fat or not, marinated, battered, chilled, dehydrated, instant, canned, reconstituted, retorted or preserve product. Examples of foodstuffs for the present invention include, without limitation: a seasonings or condiment, such as a stock, a savory cube, a powder mix, a flavored oil, a sauce, a salad dressing or a mayonnaise; a meat-based product, such as a poultry, beef or pork based product, a seafood, surimi, or a fish sausage; a soup, such as a clear soup, a cream soup, a chicken or beef soup or a tomato or asparagus soup; a carbohydrate-based product, such as instant noodles, rice, pasta, potatoes flakes or fried, noodles, pizza, tortillas or wraps; a dairy or fat product, such as a spread, a cheese, or regular or low fat margarine, a butter/margarine blend, a butter, a peanut butter, a shortening, a processed and flavored cheese; a savory product, such as a snack, a biscuit (e.g. chips or crisps) or an egg product, a potato/tortilla chip, a microwave popcorn, nuts, a pretzel, a rice cake, or a rice cracker; an imitation products, such as a dairy (e.g a reformed cheese made from oils, fats and thickeners) or seafood or meat (e.g. a vegetarian meat replacer, veggie burgers) analogue; or a pet or animal food (i.e. feed); amongst others.

In an embodiment, the edible article is one wherein the foodstuff base which comprises one or more kokumi imparting flavor compounds is selected from the group consisting of glutamic acid and a salt thereof, aspartic acid and a salt thereof, succinic acid, inosine monophosphate, guanosine monophosphate, glutathione, gamma glutamyl peptide and a mixture thereof.

The edible article of the present invention can be prepared according to methods well known in the state of the art. The appropriate ingredients and processes for the preparation of the edible articles can readily be determined by those skilled in the art according to the type of article being prepared.

All the embodiments disclosed for the compounds of formula (IA), (IB), (IC), (ID), (IE), (IF), (IG), (IH) or (IJ); or for the mixtures comprising a compound of formula (IA), (IB), (IC), (ID), (IE), (IF), (IG), (IH) or (IJ) from 86% to 99% by weight measured by quantitative proton-NMR; or for the edible composition of the invention also applies for the edible article of the fourth aspect of the invention.

As mentioned above, the fifth aspect of the invention relates to the use of a compound of formula (IA), (IB), (IC), (ID), (IE), (IF), (IG), (IH) or (IJ); or of the mixtures comprising a compound of formula (IA), (IB), (IC), (ID), (IE), (IF), (IG), (IH) or (IJ) from 86% to 99% by weight measured by quantitative proton-NMR; or alternatively an edible composition of the invention as a savoury and mouthfulness taste enhancer; particularly as a kokumi and/or umami taste enhancer. The term "taste enhancer" refers to any substance, compound or ingredient which is capable of enhancing the taste and aroma perception of taste active ingredients or compounds.

All the embodiments disclosed for the compounds of formula (IA), (IB), (IC), (ID), (IE), (IF), (IG), (IH) or (IJ); or for the mixtures comprising a compound of formula (IA), (IB), (IC), (ID), (IE), (IF), (IG), (IH) or (IJ) from 86% to 99% by weight measured by quantitative proton-NMR; or for the edible composition of the invention also applies for the edible article of the fourth aspect of the invention.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

High-pressure liquid chromatography mass spectrometry (HPLC-MS) were performed under the following conditions:

MS-spectrometer API 5500 QTrap® LC-MS/MS system (AB Sciex, Darmstadt, Germany)
UHPLC-System: Shimadzu Nexera X2 (Shimadzu Germany GmbH, Duisburg, Germany) pump: LC-30AD
degaser: DGU-20A5
autosampler: SIL-30AC
oven: CBM-20A
ionization: A) Electrospray Ionization (ESI)

scan Type: MRM
polarity: positive
software: Analyst 1.6.2 software (AB Sciex, Darmstadt, Germany)
mobile phase A: 5 mM NH₄Ac-Puffer aq., pH3
B: Acetonitril/H₂O (v/v, 95:5) 5 mM NH₄Ac-Puffer, pH 3
flowrate 0.3 mL/min
stationary phase ACQUITY UPLC@ BEH Amide (2.1×150 mm, 1.7 μm; Waters UK Ltd., Manchester, Großbritannien)
injection volume 5 μL
gradient time [min] %[B]
 0 90
 5 90
 9 65
 10 0
 13.5 0
 14.5 90
sample dissolved in water/methanol (50/50)

Ultra-high performance liquid chromatography/time-of-flight mass spectrometry (UPLC-TOF-MS) were performed under the following conditions:
LC-system Acquity UPLC Core system (Waters, Manchester, Great Britain)
MS-spectrometer Synapt G2-S HDMS Time of Flight mass spectrometer (Waters, Manchester, Great Britain)
ionization Electrospray-ionization (ESI)
software MassLynx v4.1 SCN 851 (Waters Inc.)
stationary phase BEH C18 2×150 mm, 1.7 μm (Waters UK Ltd, Manchester, Great Britain)
mobile phase A: Acetonitrile
B: 0.1% formic acid in water
flowrate 0.3 mL/min
injection volume 5 μL
gradient 5% B in 4 min to 100% B
sample dissolved in water/methanol (70/30, v/v)

Proton nuclear magnetic resonance spectroscopy (H-NMR) for the characterization of the compounds of formula (I) was performed under the following conditions:
NMR-System 1:
NMR: 400 MHz ultrashield Avance III (Bruker, Rheinstetten, Germany)
probe: Broadband Observe BBFOplus (BB. 1H) (Bruker, Rheinstetten, Germany)
Software: Topspin Version 3.2/3.0 (Bruker, Rheinstetten, Germany)
NMR-System 2:
NMR: 500 MHz ultrashield plus Avance III (Bruker, Rheinstetten, Germany)
probe: Triple Resonance Cryo Probe TCI ($^1$H/$^{13}$C/$^{15}$N) (Bruker, Rheinstetten, Germany)
Software: Topspin Version 2.1 (Bruker, Rheinstetten, Germany)

Quantitative proton nuclear magnetic resonance spectroscopy (qNMR) for determining the chemical purity of the compounds of (1) in the mixtures of the invention was performed with an ERETIC 2 (Electronic reference to access in vivo concentrations) method based on a PULCON (Pulse length-based concentration determination) method. For the calibration of the NMR spectrometer a reference (L-Tyrosine) with a known concentration (5.75 mmol/L) was measured. For the measurement of the sample a defined aliquot of the sample was dissolved in 600 μL D₂O or MeOD respectively. After measuring the sample, the concentration was calculated by means of integration a signal with a known number of protons. The NMR-system 1 was used.

1. Compounds of Formula (I)

1.1. S-((4-amino-2-methylpyrimidin-5-yl) methyl)-L-cysteine (IA)

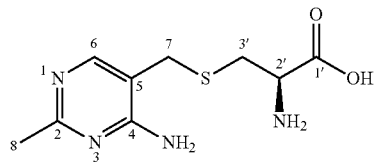

(IA)

UPLC-TOF-MS (ESI+): founded m/z=243.0915.

$^1$H NMR (400 MHz, NMR-System 1, Deuterium Oxide) δ (ppm)=8.07 [s, 1H, H—C(6)], 3.96 [t, J=5.3 Hz, 1H; H—C(2')], 3.77 [d, J=14.9 Hz, 1H, H$_b$—C(7)], 3.70 [d, J=15.0 Hz, 1H, H$_b$—C(7)], 3.00 [d, J=5.3 Hz, 2H, H—C(3')], 2.57 [s, 3H, H—C(8)]

$^{13}$C NMR (101 MHz, D2O) δ (ppm)=173.49 [C(1')], 164.31 [C(4)], 162.58 [C(2)], 142.55 [C(6)], 112.23 [C(5)], 54.13 [C(2')], 31.95 [C(3')], 28.78 [C(7)], 21.63 [C(8)].

1.2. 3-(((4-amino-2-methylpyrimidin-5-yl)methyl)thio)-5-hydroxy-pentan-2-one (IB)

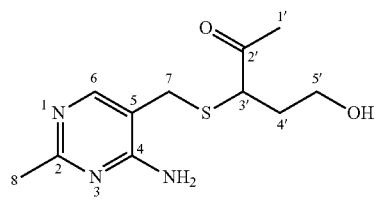

(IB)

UPLC-TOF-MS (ESI⁺): founded m/z=256.1128.

$^1$H NMR (500 MHz, NMR-System 2, Deuterium Oxide) δ (ppm)=8.07 [s, 1H, H—C(6)], 3.74-3.64 [m, 4H, H—C(7), H—C(5)], 3.54 [t, J=7.4 Hz, 1H, H—C(3')], 2.57 [s, 3H, H—C(8)], 2.30 [s, 3H, H—C(1')], 2.12 [ddt, J=14.3, 7.4 Hz, 1H H$_a$—C(4')], 1.88 [ddt, J=14.3, 7.4, 5.5 Hz, 1H, H$_b$—C(4')].

$^{13}$C NMR (101 MHz, D2O) δ (ppm)=210.66 [C(2')], 163.09 [C(4)], 162.18 [C(2)], 143.40 [C(6)], 111.47 [C(5)], 58.53 [C(5)], 50.56 [C(5)], 31.72 [C(4')], 27.54 [C(7)], 26.01 [C(1')], 21.04[C(8)].

1.3. S-((4-amino-2-methylpyrimidin-5-yl)methyl) cysteinylglycine (IC)

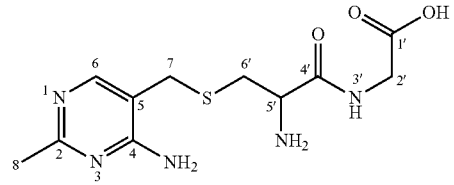

(IC)

UPLC-TOF-MS (ESI⁺): founded m/z=300.1129.

¹H NMR (400 MHz, NMR-System 1, Deuterium Oxide) δ (ppm)=8.07 [s, 1H, H—C(6)], 4.23 [t, J=6.4 Hz, 1H, H—C(5')], 3.91-3.71 [m, 4H, H—C(7), H—C(2')], 3.03 [d, J=6.4 Hz, 2H, H—C(6')], 2.58 [s, 3H. H—C(8)].

¹³C NMR (101 MHz, D2O) δ (ppm)=175.68 [C(1')], 167.94 [C(4')], 163.24 [C(4)], 161.75 [C(2)], 141.74 [C(6)], 111.20 [C(5)], 52.23 [C(5')], 43.26 [C(2')], 31.11 [C(6')], 28.38 [C(7)], 20.73 [C(8)].

1.4. 3-((((4-amino-2-methylpyrimidin-5-yl)methyl)thio)methyl)piperazine-2,5-dione (ID)

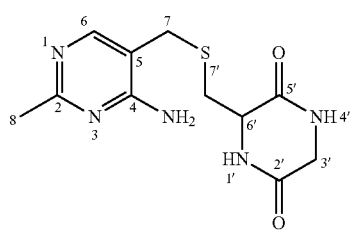

(ID)

UPLC-TOF-MS (ESI⁺): founded m/z=282.1030.

¹H NMR (400 MHz, NMR-System 1, Deuterium Oxide) δ (ppm)=8.09 [s, 1H, H—C(6)], 4.52 [dd, J=8.5, 5.2 Hz, 1H, H—C(6')], 3.82 [s, 2H, H—C(3')], 3.73 [m, 2H, H—C(7)], 2.58 [s, 3H, H—C(8)].

¹³C NMR (101 MHz, D2O) δ (ppm)=175.04 [C(5')], 171.82 [C(2')], 163.93 [C(4)], 161.64 [C(2)], 141.33 [C(6)], 111.75 [C(5)], 52.66 [C(6')], 42.90 [C(3')], 31.11 [C(6')], 28.48 [C(7)], 20.48 [C(8)]. 1.5. 3-(((4-amino-2-methylpyrimidin-5-yl)methyl)thio)pentan-2-one (IE)

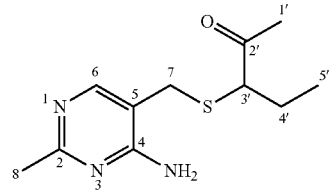

(IE)

UPLC-TOF-MS (ESI⁺): founded m/z=240.0130.

¹H NMR (400 MHz, NMR-System 1, Deuterium Oxide) δ (ppm)=7.92 [s, 1H, H—C(6)], 3.68 [d, J=14.7 Hz, 1H H$_a$—C(7)], 3.62 [d, J=14.7 Hz, 1H, H$_b$—C(7)], 3.32 [dd, J=7.35, 7.35, 1H, H—C(3')], 2.41 [s, 3H, H—C(8)], 2.20 [s, 3H, H—C(1')], 1.81 [ddq, J=14.5, 7.3, 7.3 Hz, 1H, H$_a$—C(4')], 1.67 [ddq, J=14.5, 7.4, 7.4 Hz, 1H, H$_b$—C(4')], 0.88 [dd (pt), J=7.3 Hz, 7.3 Hz 3H, H—C(5)].

¹³C NMR (101 MHz, D2O) δ (ppm)=213.25 [C(2')], 167.35 [C(4)], 162.157 [C(2)], 155.11 [C(6)], 111.58 [C(5)], 56.56 [C(3')], 29.18 [C(7)], 26.85 [C(1')], 24.16 [C(1')], 17.45[C(8)], 11.54 [C(5)].

1.6. 2-methyl-5-(((2-methylfuran-3-yl)thio)methyl)pyrimidin-4-amine (IF)

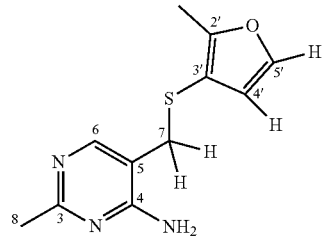

(IF)

UPLC-TOF-MS (ESI⁺): founded m/z=236.090.

¹H NMR (400 MHz, NMR-System 1, Methanol-d4) δ (ppm)=7.35 [d, J=1.9 Hz, 1H, H—C(5')], 7.29 [s, 1H, H—C(6)], 6.29 [d, J=1.9 Hz, 1H, H—C(4')], 3.65 [s, 2H, H—C(7)], 2.38 [s, 3H, H—C(8)], 1.97 [s, 3H, H—C(6')].

¹³C NMR (101 MHz, Methanol-d4) δ=166.73 [C(2)], 163.11 [C(4)], 158.23 [C(2')], 153.99 [C(6)], 142.24 [C(5)], 116.42 [C(4')], 111.94 [C(5)], 109.92 [C(3')], 34.09 [C(7)], 24.57 [C(8)], 11.24 [C(6')].

1.7. 5-(((furan-2-ylmethyl)thio)methyl)-2-methylpyrimidin-4-amine (IG)

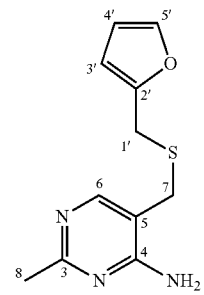

(IG)

UPLC-TOF-MS (ESI⁺): founded m/z=236.091.

¹H NMR (400 MHz, Methanol-d4) δ (ppm)=7.87 [s, 1H, H—C(6)], 7.41 [dd, J=1.9, 0.9 Hz, 1H, H—C(5')], 6.33 [dd, J=3.2, 1.9 Hz, 1H, H—C(4')], 6.20 [dd, 1H, J=3.2, 0.9 Hz, H—C(3')], 3.67 [s, 2H, H—C(1')], 3.61 [s, 2H, H—C(7)], 2.41 [s, 3H, H—C(8)].

¹³C NMR (101 MHz, Methanol-d4) δ (ppm)=166.61 [C(2)], 163.55 [C(4)], 153.56 [C(6)], 152.99 [C(2')], 143.41 [C(5')], 111.80 [C(C4')], 111.51 [C(5)], 108.62 [C(3')], 29.79 [C(7)], 28.32 [C(1')], 24.43 [C(8)].

1.8. 2-methyl-5-((methylthio)methyl)pyrimidin-4-amine (IH)

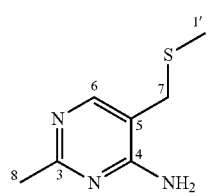

(IH)

UPLC-TOF-MS (ESI⁺): founded m/z=236.090.

¹H NMR (400 MHz, Methanol-d4) δ (ppm)=7.96 [s, 1H, H—C(6)], 3.61 [s, 2H H—C(7)], 2.46 [s, 3H, H—C(8)], 2.02 [s, 3H H—C(1')].

1.9 (4-amino-2-methylpyrimidin-5-yl)methanethiol
(IJ)

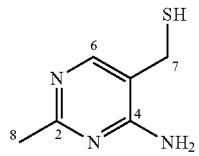

UPLC-TOF-MS (ESI⁺): founded m/z=156.056.
¹H NMR (400 MHz, Methanol-d4) δ (ppm)=7.83 [s, 1H, H—C(6)], 3.54 [s, 2H, H—C(7)], 2.43 [s, 3H, H—C(8)].

2. Mixtures Comprising an Amount from 86% to 99% by Weight Measured by Quantitative Proton-NMR of a Compound of Formula (IA), (IB), (IC), (ID), (IE), (IF), (IG), (IH) and (IJ)

2.1. Preparation of a Mixture Comprising an Amount from 86% to 99% by Weight Measured by Quantitative Proton-NMR of a Compound of Formula (IA) or a Compound of Formula (IB) and Characterization of the Compounds of Formula (IA) and (IB)

2.1.1. Model Reaction System of Thiamine and Cysteine 1 mmol (337 mg) of Thiamine Hydrochloride (Sigma Aldrich, Steinheim, Germany) and 1 mmol (121 mg) of L-Cysteine (Sigma Aldrich, Steinheim, Germany) were dissolved in 10 mL 0.1M KH₂PO₄-buffer. The mixture was heated in an aluminum block at 120° C. for 5 hours while stirring in a closed pyrex glass.

2.1.2. Sequential Solvent Extraction

The mixture obtained in section 2.1.1. was extracted twice with 10 mL ethyl acetate. The organic layers were combined, and the solvent removed in a vacuum to yield the ethyl acetate fraction. The aqueous layer was named the water fraction.

2.1.3. Preparation of the Mixture Comprising an Amount from 86% to 99% by Weight Measured by Quantitative Proton-NMR of a Compound of Formula (IA) from the Water Fraction Thiamine-Cysteine Model Reaction System The water fraction obtained in section 2.1.2. was diluted 1:2 with water, membrane-filtered (0.45 μm) and separated by means of preparative RP-HPLC on a Phenyl-Hexyl column. The conditions are listed in the following table.

| stationary phase | Phenyl-Hexyl (250 × 10.00 mm; Phenomenex Aschaffenburg) |
|---|---|
| flow rate | 20 mL/min |
| detection | UV 254 nm |
| eluents | A: 0.1% formic acid in water |
|  | B: acetonitrile |

| gradient | time [min] | solvent B [%] |
|---|---|---|
|  | 0 | 0 |
|  | 5 | 0 |
|  | 10 | 40 |
|  | 12 | 100 |
|  | 14 | 100 |
|  | 17 | 0 |
|  | 20 | 0 |

Nine fractions were separated as shown in FIG. 1A. The yield of each fraction is shown in the following table:

| Fraction | yield [%] |
|---|---|
| 1 | 26.32% |
| 2 | 5.70% |
| 3 | 15.13% |
| 4 | 15.14% |
| 5 | 14.80% |
| 6 | 1.29% |
| 7 | 16.26% |
| 8 | 4.86% |
| 9 | 0.51% |

The lyophilized HPLC-fraction 2 was dissolved in water membrane-filtered (0.45 μm) and separated by means of semi preparative RP-HPLC on Pentafluorphenyl column using the following conditions.

| stationary phase | Luna 5μ PFP(2) (250 × 10.00 mm i.d., 100 Å; Phenomenex, Aschaffenburg) |
|---|---|
| flow rate | 4 mL/min |
| detection | ELSD |
| eluents | A: 0.1% formic acid in water |
|  | B: methanol |

| gradient | time [min] | solvent B [%] |
|---|---|---|
|  | 0 | 0 |
|  | 5 | 0 |
|  | 6 | 30 |
|  | 8 | 30 |
|  | 9 | 0 |
|  | 12 | 0 |

Figure 1B:
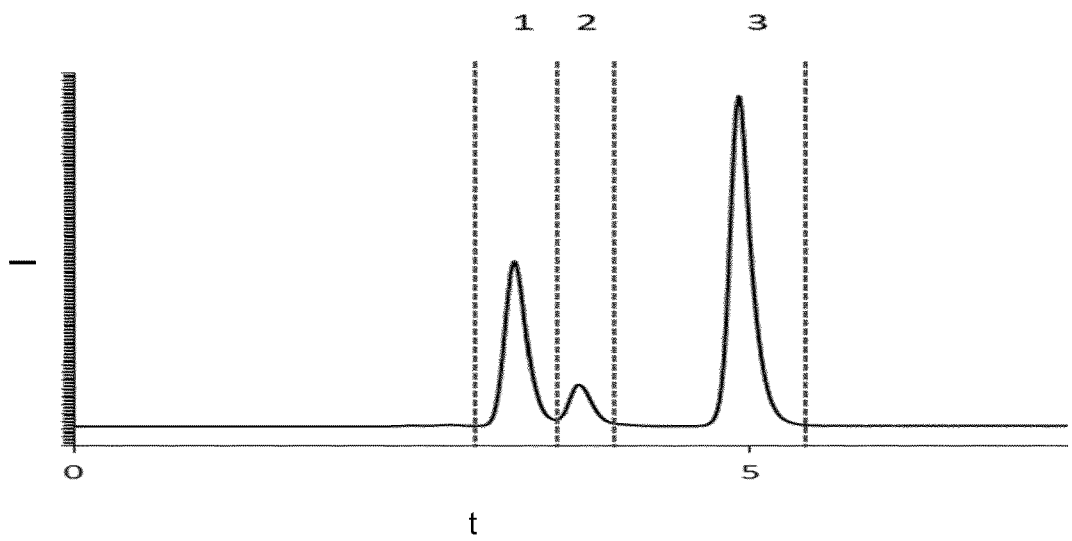
FIG. 1B refers to the three fractions obtained by means of semi preparative RP-HPLC on Pentafluorphenyl column lyophilized HPLC-fraction 2 for the preparation of the mixture comprising an amount from 86% to 99% area/area measured by HPLC-MS of a compound of formula (IA). Units of the scheme are as follows: "I" is intensity in [mAU] and "t" is time in minutes.

Three fractions were separated as shown in FIG. 1B.

The lyophilized HPLC-fraction 2-1 was dissolved in water membrane-filtered (0.45 μm) and separated by means of semi preparative HILIC on TSKgel Amid-80 column using the following conditions.

| stationary phase | TSKgel Amid-80 (300 × 21.5 mm i.d., 10 μm; Tosho Bioscience, Griesheim) |
|---|---|
| flow rate | 8 mL/min |
| detection | ELSD |
| eluents | A: 0.1% formic acid in water |
|  | B: methanol |

| gradient | time [min] | solvent B [%] |
|---|---|---|
|  | 0 | 75 |
|  | 4 | 75 |
|  | 27 | 0 |
|  | 35 | 0 |
|  | 38 | 75 |
|  | 40 | 75 |

Figure 1C:
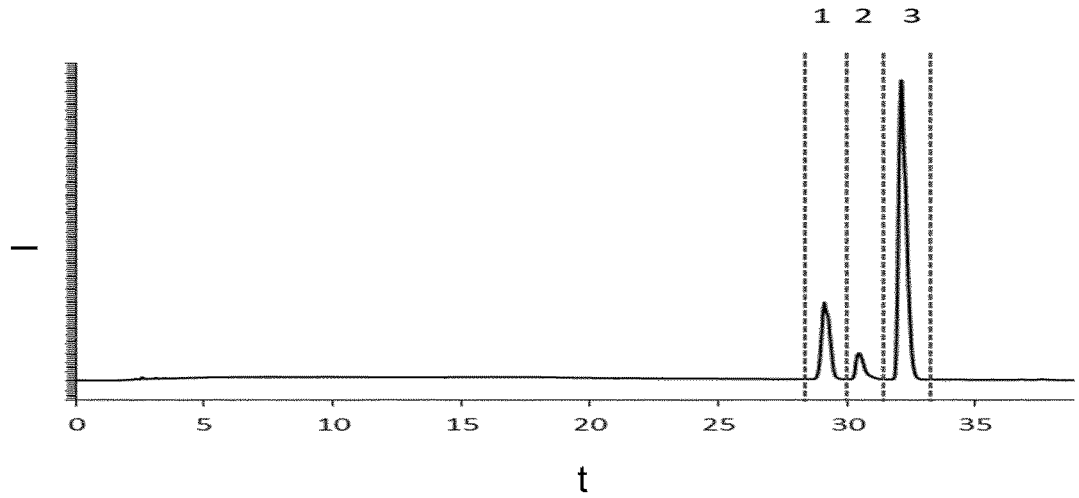
FIG. 1C refers to the three fractions obtained by means of semi preparative HILIC on TSKgel Amid-80 column lyophilized HPLC-fraction 2.1 for the preparation of the mixture comprising an amount from 86% to 99% area/area measured by HPLC-MS of a compound of formula (IA). Units of the scheme are as follows: "I" is intensity in [mAU] and "t" is time in minutes.

Three fractions were separated as shown in FIG. 1C.

The mixture comprising an amount from 86% to 99% by weight measured by quantitative proton-NMR of a compound of formula (IA) of the present invention is the fraction 2-1-3 obtained by means of the semi preparative HILIC on TSKgel Amid-80 column as defined above. The compound of formula (IA) was characterized from fraction 2-1-3 by means of UHPLC/TOF/MS (cf. section 1.1.).

2.1.4. Preparation of the Mixture Comprising an Amount from 86% to 99% by Weight Measured by Quantitative Proton-NMR of a Compound of Formula (IB)

The ethyl acetate fraction obtained in section 2.1.2. was dissolved in 50% aqueous acetonitrile, membrane-filtered (0.45 µm) and separated by means of preparative RP-HPLC on a MonoChrom column. The conditions are listed in the following table.

| stationary phase | MonoChrom MS 5u (250 × 21.2 mm i.d.; Varian, Darmstadt) |
|---|---|
| flow rate | 20 mL/min |
| detection | UV 254 nm |
| eluents | A: 0.1% formic acid in water |
| | B: acetonitrile |

| gradient | time [min] | solvent B [%] |
|---|---|---|
| | 0 | 0 |
| | 2 | 0 |
| | 14 | 40 |
| | 15 | 100 |
| | 16 | 100 |
| | 17 | 0 |
| | 20 | 0 |

Figure 2A:
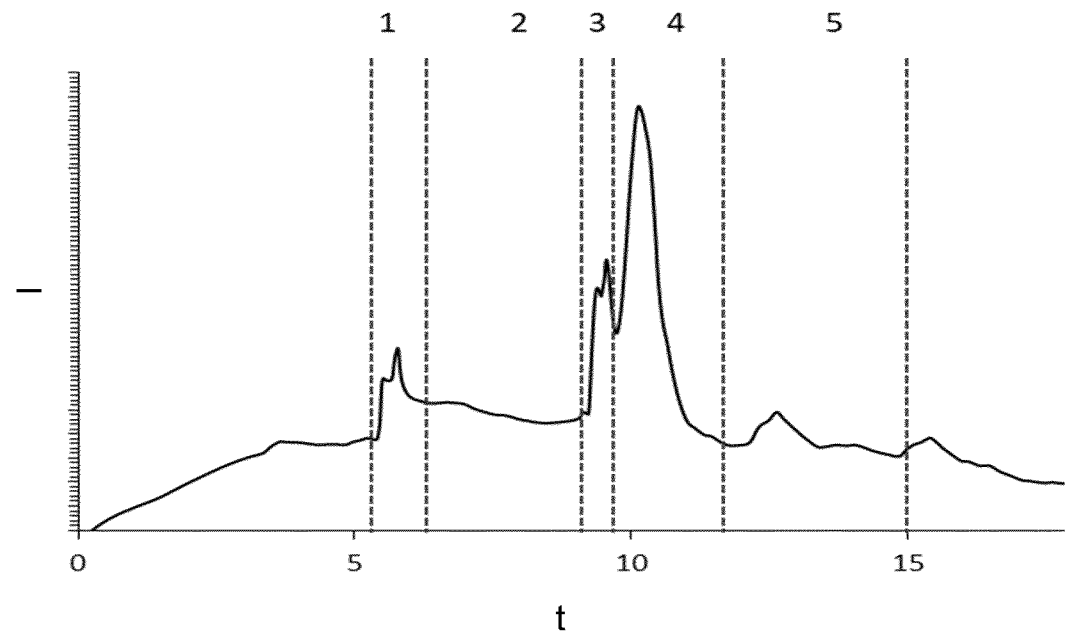
FIG. 2A refers to the five fractions obtained by means of preparative RP-HPLC on a MonoChrom column of ethylacetate fraction obtained in section 2.1.2 for the preparation of the mixture comprising an amount from 86% to 99% area/area measured by HPLC-MS of a compound of formula (IB). Units of the scheme are as follows: "I" is intensity in [mAU] and "t" is time in minutes.

Five fractions were separated as shown in FIG. 2A. The yield of each fraction is shown in the following table:

| Fraction | yield [%] |
|---|---|
| 1 | 18.00% |
| 2 | 1.00% |
| 3 | 2.00% |
| 4 | 5.00% |
| 5 | 40.00% |
| 6 | 33.00% |

The lyophilized HPLC-fraction 5 was dissolved in 50% aqueous acetonitrile membrane-filtered (0.45 µm) and separated by means of semi preparative RP-HPLC on Pentafluorphenyl column using the following conditions.

| stationary phase | Luna 5µ PFP (250 × 10.00 mm i.d., 100 Å; Phenomenex, Aschaffenburg) |
|---|---|
| flow rate | 20 mL/min |
| detection | ELSD |
| eluents | A: 0.1% formic acid in water |
| | B: methanol |

| gradient | time [min] | solvent B [%] |
|---|---|---|
| | 0 | 25 |
| | 2 | 25 |
| | 5 | 45 |
| | 8 | 65 |
| | 9 | 100 |
| | 11 | 25 |
| | 13 | 25 |

Figure 2B:
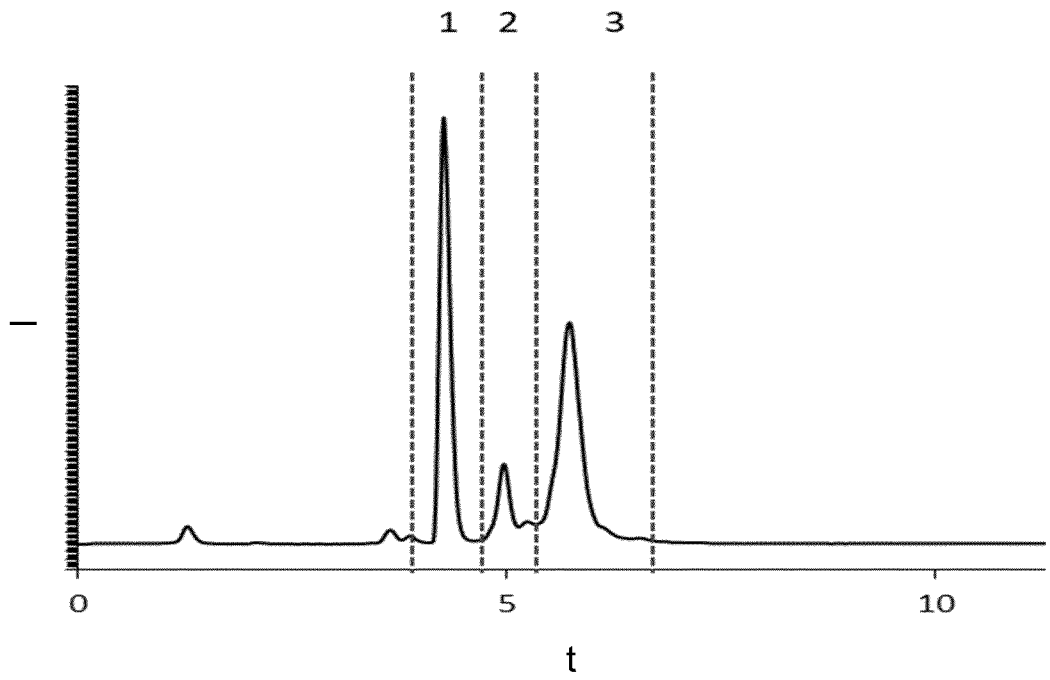
FIG. 2B refers to the three fractions obtained by means of semi preparative RP-HPLC on Pentafluorphenyl column obtained from the lyophilized HPLC-fraction 5 for the preparation of the mixture comprising an amount from 86% to 99% area/area measured by HPLC-MS of a compound of formula (IB). Units of the scheme are as follows: "I" is intensity in [mAU] and "t" is time in minutes.

Three fractions were separated as shown in FIG. 2B.

The mixture comprising an amount from 86% to 99% by weight measured by quantitative proton-NMR of a compound of formula (IB) of the present invention is the fraction 5-3 obtained by means of the semi preparative RP-HPLC on Pentafluorphenyl column as defined above. The compound of formula (IB) was characterized from fraction 5-3 by means of UHPLC/TOF/MS (cf. section 1.2.).

2.2. Preparation of the Mixture Comprising an Amount from 86% to 99% by Weight Measured by Quantitative Proton-NMR of a Compound of Formula (IC) or a Compound of Formula (ID) and Characterization of the Compounds of Formula (IC) and (ID)

2.2.1. Model Reaction System of Thiamine and Glutathione 1 mmol (337 mg) of Thiamine Hydrochloride (Sigma Aldrich, Steinheim, Germany) and 1 mmol (307 mg) of Glutathione (Sigma Aldrich, Steinheim, Germany) were dissolved in 10 mL 0.1M $KH_2PO_4$-buffer. The mixture was heated in an aluminum block at 120° C. for 5 hours while stirring in a closed pyrex glass.

2.2.2. Preparation of the Mixture Comprising an Amount from 86% to 99% by Weight Measured by Quantitative Proton-NMR of a Compound of Formula (IC) or a Compound of Formula (ID) from the Thiamine-Cysteine Model Reaction System The reaction system obtained in section 2.2.1. was diluted 1:2 with water, membrane-filtered (0.45 µm) and separated by means of preparative RP-HPLC on a Phenyl-Hexyl column. The conditions are listed in the following table.

| stationary phase | Phenyl-Hexyl (250 × 10.00 mm; Phenomenex Aschaffenburg) |
|---|---|
| flow rate | 20 mL/min |
| detection | UV 254 nm |
| eluents | A: 0.1% formic acid in water |
| | B: acetonitrile |

| gradient | time [min] | solvent B [%] |
|---|---|---|
| | 0 | 0 |
| | 5 | 0 |
| | 10 | 40 |
| | 12 | 100 |
| | 14 | 100 |
| | 17 | 0 |
| | 20 | 0 |

Figure 3:
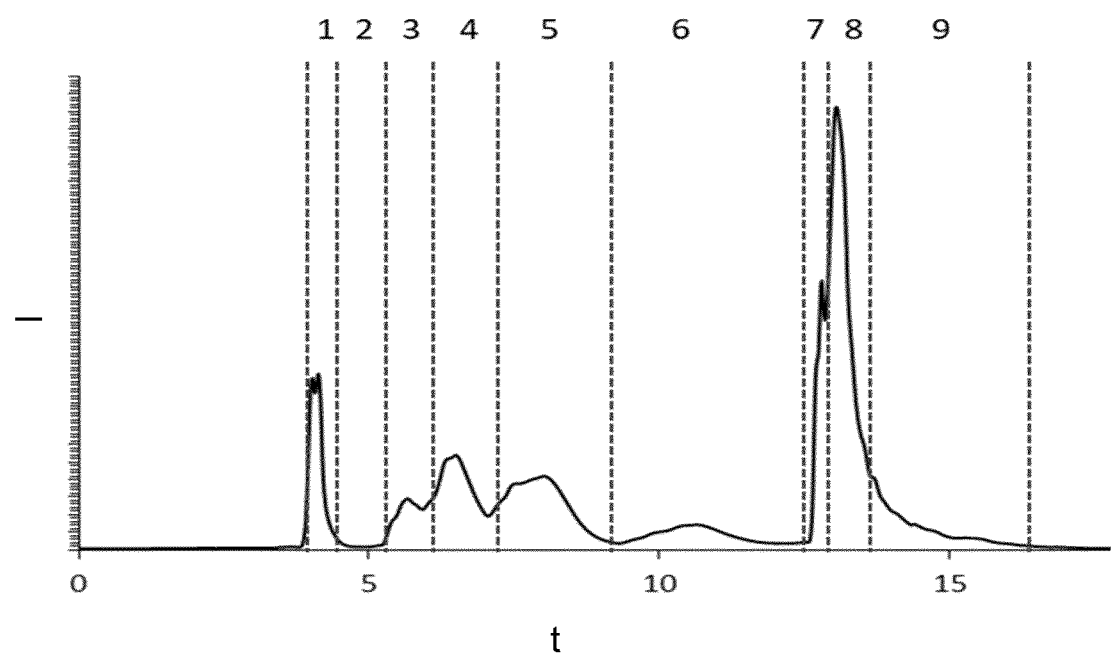
FIG. 3. refers to the nine fractions obtained by means of preparative RP-HPLC on a Phenyl-Hexyl column of the water fraction obtained in section 2.2.2 for the preparation of the mixture comprising an amount from 86% to 99% area/area measured by HPLC-MS of a compound of formula (IC) or (ID). Units of the scheme are as follows: "I" is intensity in [mAU] and "t" is time in minutes.

Nine fractions were separated as shown in FIG. 3. The yield of each fraction is shown in the following table:

| Fraction | yield [%] |
|---|---|
| 1 | 26.32% |
| 2 | 5.70% |
| 3 | 15.13% |
| 4 | 15.14% |
| 5 | 14.80% |
| 6 | 1.29% |
| 7 | 16.26% |
| 8 | 4.86% |
| 9 | 0.51% |

The mixture comprising an amount from 86% to 99% by weight measured by quantitative proton-NMR of a compound of formula (IC) of the present invention is the fraction 3 obtained by means of the preparative RP-HPLC on a Phenyl-Hexyl column as defined above. The compound of formula (IC) was characterized from fraction 3 by means of UHPLC/TOF/MS (cf. section 1.3.).

And, the mixture comprising an amount from 86% to 99% by weight measured by quantitative proton-NMR of a compound of formula (ID) of the present invention is the fraction 6 obtained by means of the preparative RP-HPLC on a Phenyl-Hexyl column as defined above. The compound of formula (ID) was characterized from fraction 6 by means of UHPLC/TOF/MS (cf. section 1.4.).

2.3. Preparation of the Mixture Comprising an Amount from 86% to 99% by Weight Measured by Quantitative Proton-NMR of a Compound of Formula (IE) and Characterization of the Compound of Formula (IE)

2.3.1. Reaction System

50 µmol (18 mg) 4-Amino-5-(bromomethyl)-2-methylpyrimidin Hydrobromide (Toronto Research Chemicals, Toronto, Canada) were dissolved in 500 µL water free dimethylformamide (DMF) afterwards 100 µmol 3-Mercapto-2-pentanone (Alfa Aesar, Karlsruhe, Germany) were added. The system was stirred in argon atmosphere for 10 hours at 50° C. in a closed pyrex glass.

2.3.2. Preparation of the Mixture Comprising an Amount from 86% to 99% by Weight Measured by Quantitative Proton-NMR of a Compound of Formula (IE) from the Reaction System The reaction mixture obtained in section 2.3.1. was diluted with water, membrane-filtered (0.45 µm) and separated by means of semi preparative RP-HPLC on Monochrom column using the following conditions:

| stationary phase | MonoChrom MS 5u (250 × 21.2 mm i.d.; Varian, Darmstadt) |
| --- | --- |
| flow rate | 20 mL/min |
| detection | UV 254 nm |
| eluents | A: 0.1% formic acid in water B: acetonitrile |

| gradient | time [min] | solvent B [%] |
| --- | --- | --- |
| | 0 | 0 |
| | 2 | 0 |
| | 14 | 40 |
| | 15 | 100 |
| | 16 | 100 |
| | 17 | 0 |
| | 20 | 0 |

Figure 4:
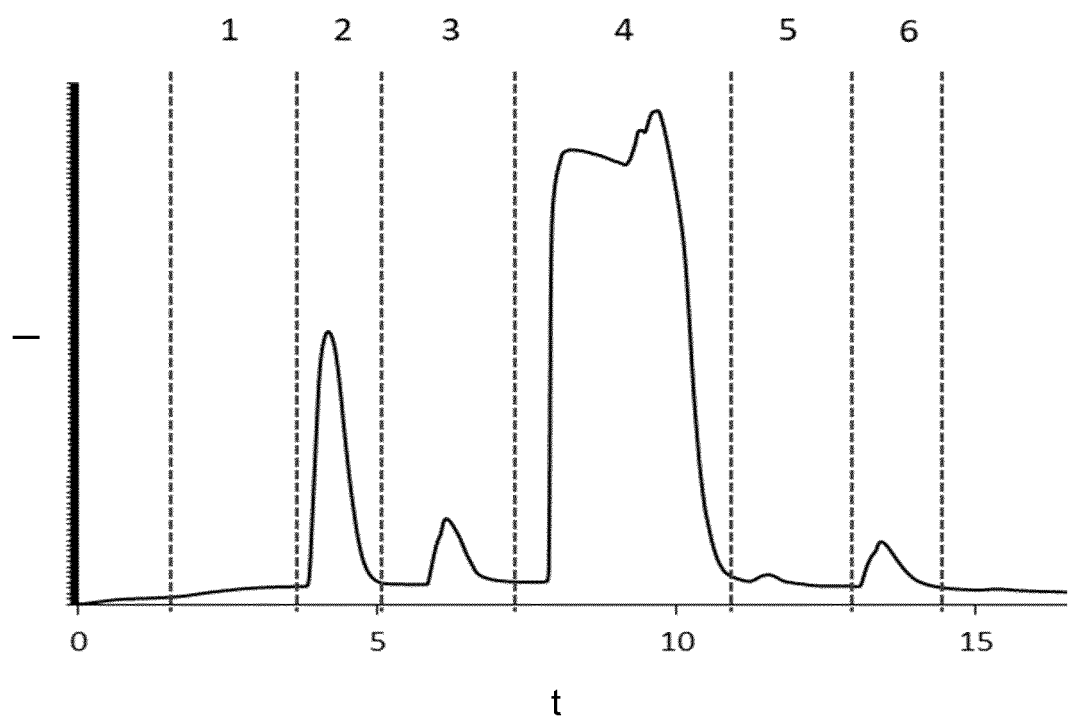
FIG. 4. refers to the six fractions obtained by means of semi preparative RP-HPLC on Monochrom column of reaction mixture obtained in section 2.3.2 for the preparation of the mixture comprising an amount from 86% to 99% area/area measured by HPLC-MS of a compound of formula (IE). Units of the scheme are as follows: "I" is intensity in [mAU] and "t" is time in minutes.

Six fractions were separated as shown in FIG. 4.

The mixture comprising an amount from 86% to 99% by weight measured by quantitative proton-NMR of a compound of formula (IE) of the present invention is the fraction 6 obtained by means of the semi preparative RP-HPLC on Monochrom column as defined above. The compound of formula (IE) was characterized from fraction 6 by means of UHPLC/TOF/MS (cf. section 1.5.).

2.4. Preparation of the Mixture Comprising an Amount from 86% to 99% by Weight Measured by Quantitative Proton-NMR of a Compound of Formula (IF) and Characterization of the Compound of Formula (IF)

2.4.1. Reaction System 1 mmol (337 mg) of Thiamine Hydrochloride (Sigma Aldrich, Steinheim, Germany) and 1 mmol (114 mg) of 2-Methyl-3-furanthiol (MFT) (Sigma Aldrich, Steinheim, Germany) were dissolved in 10 mL 0.1M $KH_2PO_4$-buffer (pH 7). The mixture was heated in an aluminum block at 120° C. for 5 hours while stirring in a closed pyrex glass.

2.4.2. Preparation of the Mixture Comprising an Amount from 86% to 99% by Weight Measured by Quantitative Proton-NMR of a Compound of Formula (IF) from the Thiamine-2-Methyl-3-Furanthiol Model Reaction System The reaction system obtained in section 2.4.1. was diluted 1:2 with water, membrane-filtered (0.45 µm) and separated by means of preparative RP-HPLC on a Monochrom column. The conditions are listed in the following table.

| stationary phase | MonoChrom MS 5u (250 × 21.2 mm i.d.; Varian, Darmstadt) |
| --- | --- |
| flow rate | 20 mL/min |
| detection | UV 254 nm |
| eluents | A: 0.1% formic acid in water B: acetonitrile |

| gradient | time [min] | solvent B [%] |
| --- | --- | --- |
| | 0 | 0 |
| | 2 | 0 |
| | 14 | 40 |
| | 15 | 100 |
| | 16 | 100 |
| | 17 | 0 |
| | 20 | 0 |

Figure 5A:
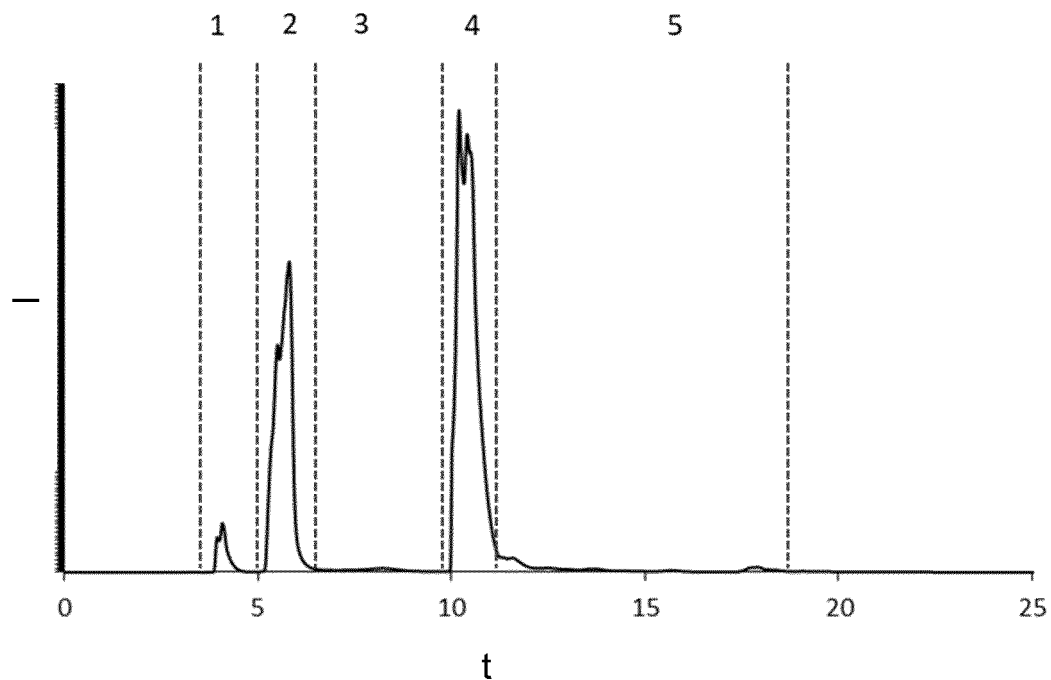
FIG. 5A. refers to the five fractions obtained by means of semi preparative RP-HPLC on Monochrom column of reaction mixture obtained in section 2.4.2 for the preparation of the mixture comprising an amount from 86% to 99% area/area measured by HPLC-MS of a compound of formula (IF). Units of the scheme are as follows: "I" is intensity in [mAU] and "t" is time in minutes.

Five fractions were separated as shown in FIG. 5A.

The lyophilized HPLC-fraction 4 was dissolved in 50% aqueous Acetonitrile membrane-filtered (0.45 µm) and separated by means of semipreparative RP-HPLC on Pentafluorphenyl column using the following conditions:

| stationary phase | Luna PFP (2) (250 × 21.2 mm i.d., 5 µm; Phenomenex, Aschaffenburg) |
| --- | --- |
| flow rate | 4 mL/min |
| detection | UV 254 nm |
| eluents | A: 0.1% formic acid in water B: acetonitrile |

| gradient | time [min] | solvent B [%] |
| --- | --- | --- |
| | 0 | 12 |
| | 2 | 12 |
| | 13 | 18 |
| | 15 | 40 |
| | 16 | 12 |
| | 17 | 12 |

Figure 5B:
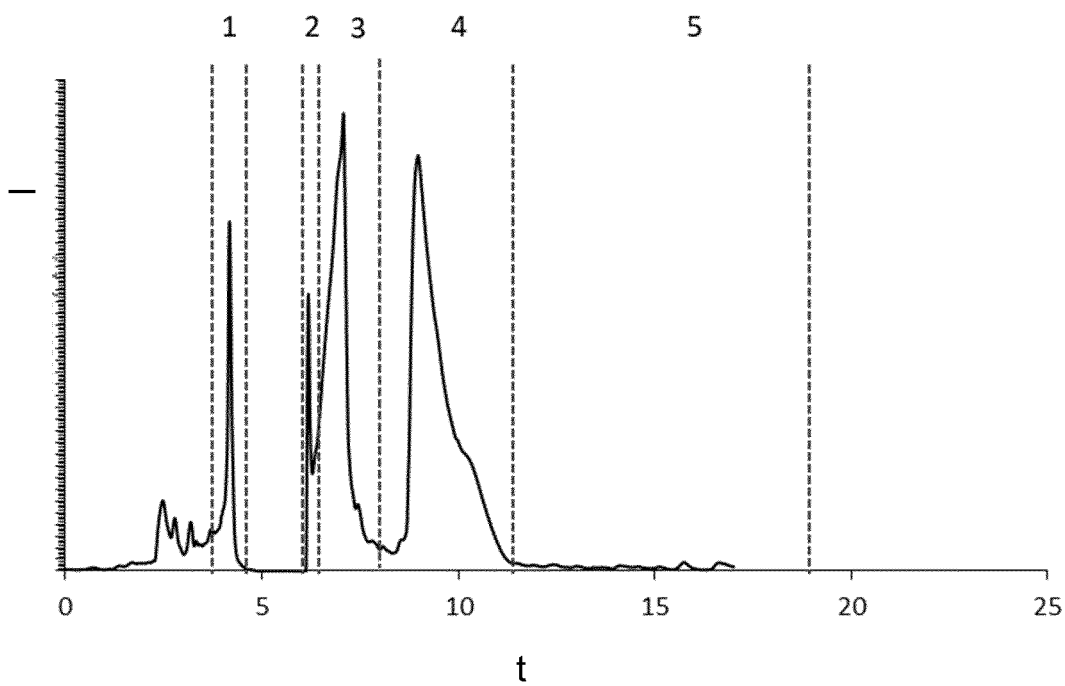
FIG. 5B. refers to fraction 4 obtained by means of preparative RP-HPLC on a Phenylfluorphenyl column obtained in section 2.4.2. for the preparation of the mixture comprising an amount from 86% to 99% area/area measured by HPLC-MS of a compound of formula (IF). Units of the scheme are as follows: "I" is intensity in [mAU] and "t" is time in minutes.

Five fractions were separated as shown in FIG. 5B.

The mixture comprising an amount from 86% to 99% by weight measured by quantitative proton-NMR of a compound of formula (IF) of the present invention is the fraction 4 obtained by means of the preparative RP-HPLC on a Pentafluorphenyl column as defined above. The compound of formula (IF) was characterized from fraction 4 by means of UHPLC/TOF/MS (cf. section 1.6.).

2.5. Preparation of the Mixture Comprising an Amount from 86% to 99% by Weight Measured by Quantitative Proton-NMR of a Compound of Formula (IG) and Characterization of the Compound of Formula (IG)

2.5.1. Reaction System 1 mmol (337 mg) of Thiamine Hydrochloride (Sigma Aldrich, Steinheim, Germany) and 1 mmol (114 mg) of 2-Furanmethanethiol (FFT) (Sigma Aldrich, Steinheim, Germany) were dissolved in 10 mL 0.1M $KH_2PO_4$-buffer (pH 7). The mixture was heated in an aluminum block at 120° C. for 5 hours while stirring in a closed pyrex glass.

2.5.2. Preparation of the Mixture Comprising an Amount from 86% to 99% by Weight Measured by Quantitative Proton-NMR of a Compound of Formula (IG) from the Thiamine-2-Furanmethanethiol Model Reaction System The reaction system obtained in section 2.5.1. was diluted 1:2 with water, membrane-filtered (0.45 µm) and separated by means of preparative RP-HPLC on a Monochrom column. The conditions are listed in the following table.

| stationary phase | MonoChrom MS 5u (250 × 21.2 mm i.d.; Varian, Darmstadt) |
|---|---|
| flow rate | 20 mL/min |
| detection | UV 254 nm |
| eluents | A: 0.1% formic acid in water B: acetonitrile |

| gradient | time [min] | solvent B [%] |
|---|---|---|
| | 0 | 0 |
| | 2 | 0 |
| | 14 | 40 |
| | 15 | 100 |
| | 16 | 100 |
| | 17 | 0 |
| | 20 | 0 |

Figure 6A:
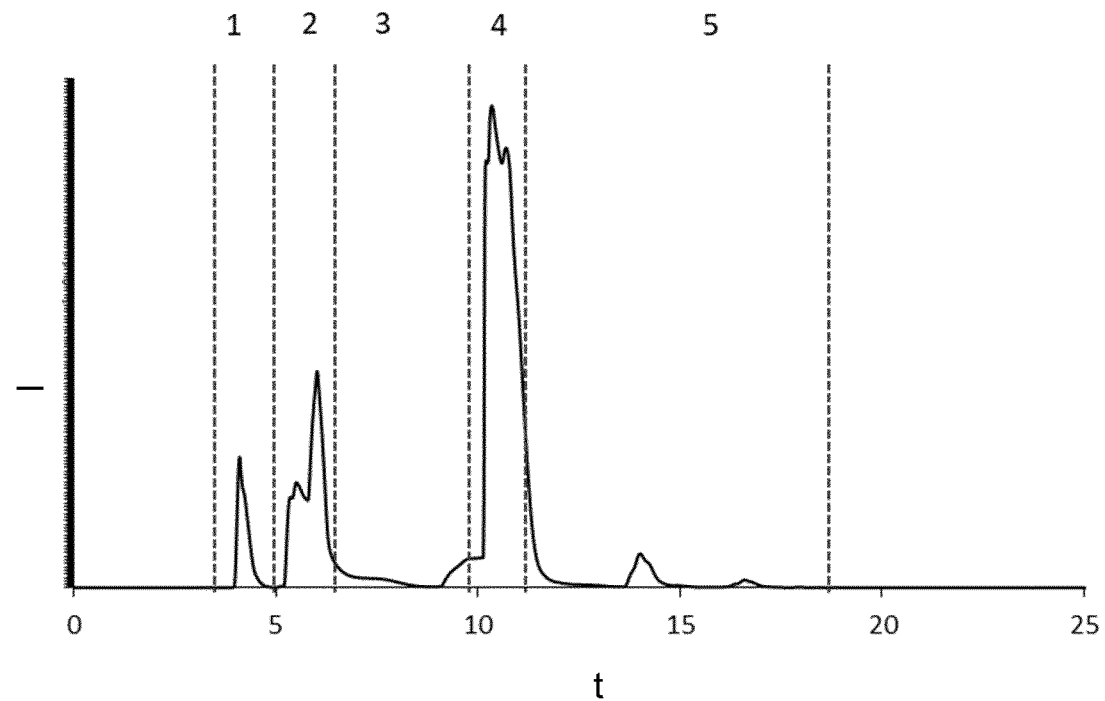
FIG. 6A. refers to the five fractions obtained by means of semi preparative RP-HPLC on Monochrom column of reaction mixture obtained in section 2.5.2 for the preparation of the mixture comprising an amount from 86% to 99% area/area measured by HPLC-MS of a compound of formula (IG). Units of the scheme are as follows: "I" is intensity in [mAU] and "t" is time in minutes.

Five fractions were separated as shown in FIG. 6A.

The lyophilized HPLC-fraction 4 was dissolved in 50% aqueous Acetonitrile membrane-filtered (0.45 µm) and separated by means of semipreparative RP-HPLC on Pentafluorphenyl column using the following conditions:

| stationary phase | Luna PFP (2) (250 × 21.2 mm i.d., 5 µm; Phenomenex, Aschaffenburg) |
|---|---|
| flow rate | 4 mL/min |
| detection | UV 254 nm |
| eluents | A: 0.1% formic acid in water B: acetonitrile |

| gradient | time [min] | solvent B [%] |
|---|---|---|
| | 0 | 12 |
| | 2 | 12 |
| | 13 | 18 |
| | 15 | 40 |
| | 16 | 12 |
| | 17 | 12 |

Figure 6B:
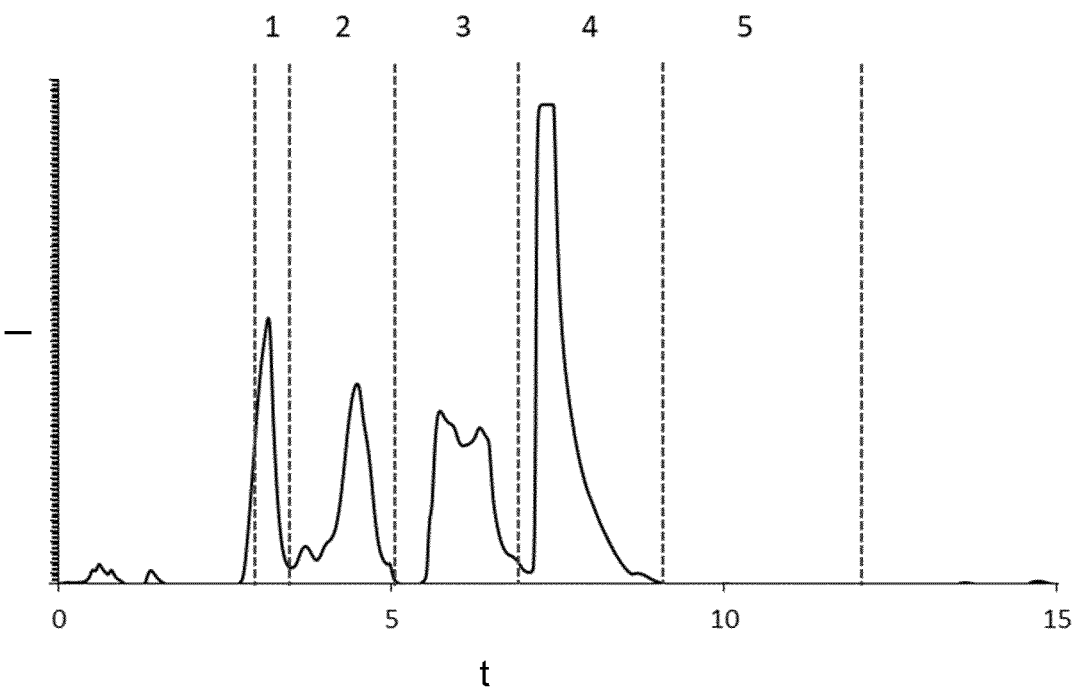
FIG. 6B. refers to fraction 4 obtained by means of preparative RP-HPLC on a Phenylfluorphenyl column obtained in section 2.4.2. for the preparation of the mixture comprising an amount from 86% to 99% area/area measured by HPLC-MS of a compound of formula (IG). Units of the scheme are as follows: "I" is intensity in [mAU] and "t" is time in minutes.

Five fractions were separated as shown in FIG. 6B.

The mixture comprising an amount from 86% to 99% by weight measured by quantitative proton-NMR of a compound of formula (IG) of the present invention is the fraction 4 obtained by means of the preparative RP-HPLC on a Pentafluorphenyl column as defined above. The compound of formula (IG) was characterized from fraction 4 by means of UHPLC/TOF/MS (cf. section 1.7.).

2.7. Preparation of the Mixture Comprising an Amount from 86% to 99% by Weight Measured by Quantitative Proton-NMR of a Compound of Formula (IH) and Characterization of the Compound of Formula (IH)

2.7.1. Reaction System

50 µmol (18 mg) of 4-amino-5-(bromomethyl)-2-methylpyrimidin Hydrobromide (Toronto Research Chemicals, Toronto, Canada) were dissolved in 500 µL water free of DMF. To the mixture thus obtained 100 µmol of sodium thiomethoxide (Sigma Aldrich, Steinheim, Germany) were added. The resulting mixture was stirred in argon atmosphere for 15 hours at 50° C. in a closed pyrex glass.

2.7.2. Preparation of the Mixture Comprising an Amount from 86% to 99% by Weight Measured by Quantitative Proton-NMR of a Compound of Formula (IH)

The reaction system obtained in section 2.7.1. was diluted 1:2 with water, membrane-filtered (0.45 µm) and separated by means of preparative RP-HPLC on a Monochrom column. The conditions are listed in the following table.

| stationary phase | MonoChrom MS 5u (250 × 21.2 mm i.d.; Varian, Darmstadt) |
|---|---|
| flow rate | 20 mL/min |
| detection | UV 254 nm |
| eluents | A: 0.1% formic acid in water B: acetonitrile |

| gradient | time [min] | solvent B [%] |
|---|---|---|
| | 0 | 0 |
| | 2 | 0 |
| | 14 | 40 |
| | 15 | 100 |
| | 16 | 100 |
| | 17 | 0 |
| | 20 | 0 |

Figure 7A:
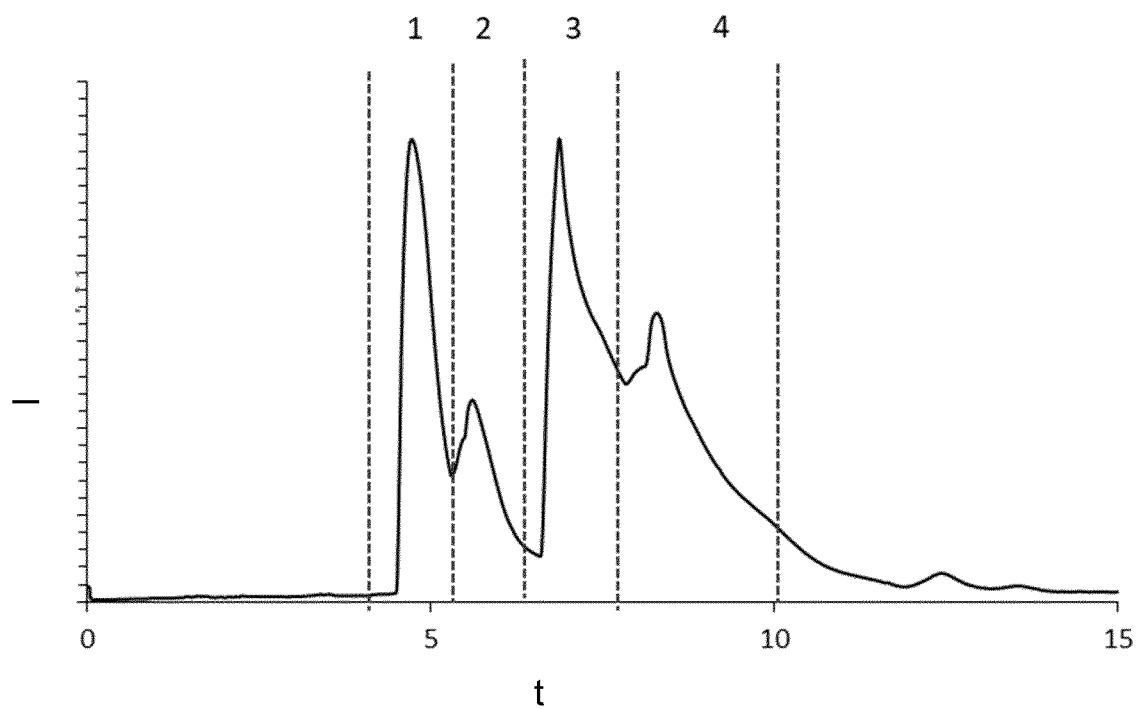
FIG. 7A. refers to the four fractions obtained by means of preparative RP-HPLC on a Monochrom column of reaction mixture obtained in section 2.7.2. for the preparation of the mixture comprising an amount from 86 to 99% area/area measured by HPLC-MS of a compound of formula (IH). Units of scheme are as follows: "I" is intensity in [mAU] and "t" is time in minutes.

Four fractions were separated as shown in FIG. 7A.

The lyophilized HPLC-fraction 4 was dissolved in 50% aqueous Acetonitrile membrane-filtered (0.45 µm) and separated by means of semipreparative RP-HPLC on Hydro-RP column using the following conditions:

| stationary phase | Hydro RP (250 × 21.2 mm i.d., 5 µm; Phenomenex, Aschaffenburg) |
|---|---|
| flow rate | 4 mL/min |
| detection | UV 254 nm |
| eluents | A: 0.1% formic acid in water B: acetonitrile |

| Gradient | time [min] | solvent B [%] |
|---|---|---|
| | Isocratic 8 | |

Figure 7B:
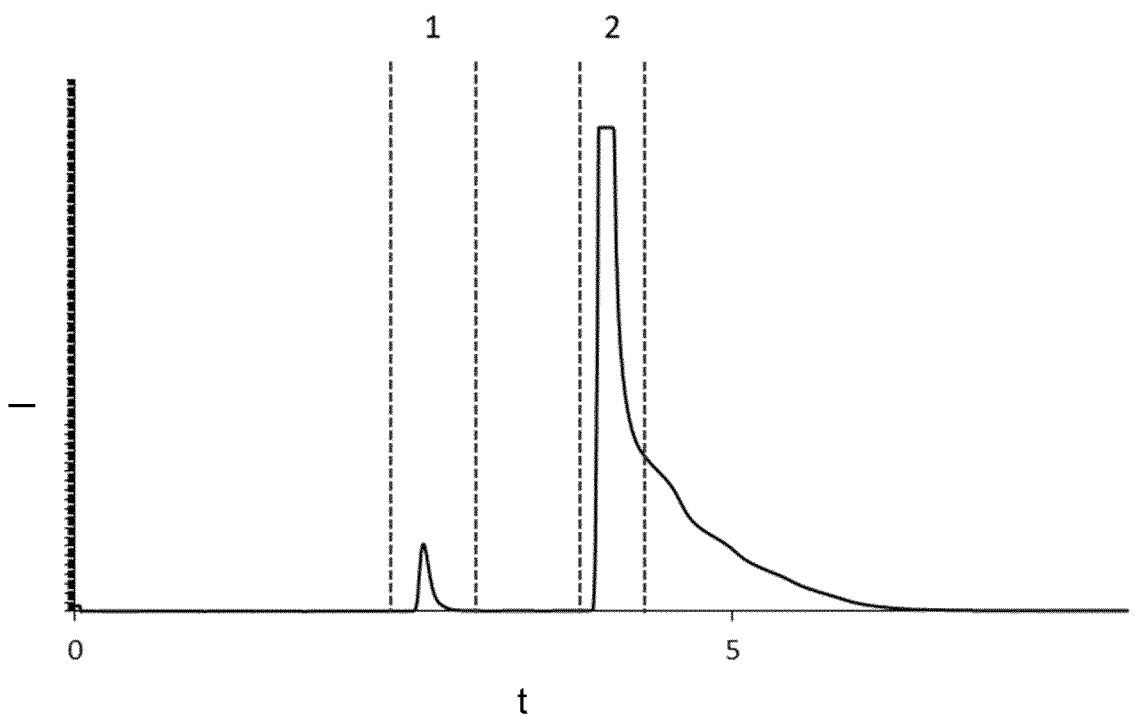
FIG. 7B. Refers to fraction 4 obtained by means of preparative RP-HPLC on a hydro RP column obtained in section 2.7.2. for the preparation of the compound of formula (IH). Units of scheme are as follows: "I" is intensity in [mAU] and "t" is time in minutes.

Two fractions were separated as shown in FIG. 7B.

The mixture comprising an amount from 86% to 99% by weight measured by quantitative proton-NMR of a compound of formula (IH) of the present invention is the fraction 2 obtained by means of the preparative RP-HPLC on a Hydro RP column as defined above. The compound of formula (IH) was characterized from fraction 2 by means of UHPLC/TOF/MS (cf. section 1.8.).

2.8. Preparation of the Mixture Comprising an Amount from 86% to 99% by Weight Measured by Quantitative Proton-NMR of a Compound of Formula (IJ) and Characterization of the Compound of Formula (IJ)

2.8.1. Reaction System

4-Amino-5-(bromomethyl)-2-methylpyrimidin Hydrobromide (Toronto Research Chemicals, Toronto, Canada) were dissolved in 500 µL water free DMF afterwards 100 µmol Sodium Thioacetate (Sigma Aldrich, Steinheim, Germany) were added. The system was stirred in argon atmosphere for 15 hours at 50° C. in a closed pyrex glass. Afterwards 5 mL of a 3 M NaOH-solution were added, and the mixture was stirred for further 4 hours. After neutralization with a 1 M HCl-solution mixture was separated by means of preparative HPLC.

2.8.2. Preparation of the Mixture Comprising an Amount from 86% to 99% by Weight Measured by Quantitative Proton-NMR of a Compound of Formula (IJ)

The reaction system obtained in section 2.8.1. was diluted 1:2 with water, membrane-filtered (0.45 µm) and separated by means of preparative RP-HPLC on a MonoChrom column. The conditions are listed in the following table.

| stationary phase | MonoChrom MS 5u (250 × 21.2 mm i.d.; Varian, Darmstadt) | |
|---|---|---|
| flow rate | 20 mL/min | |
| detection | UV 254 nm | |
| eluents | A: 0.1% formic acid in water B: acetonitrile | |
| gradient | time [min] | solvent B [%] |
| | 0 | 2 |
| | 5 | 2 |
| | 10 | 15 |
| | 11 | 40 |
| | 12 | 2 |
| | 17 | 2 |

Figure 8:
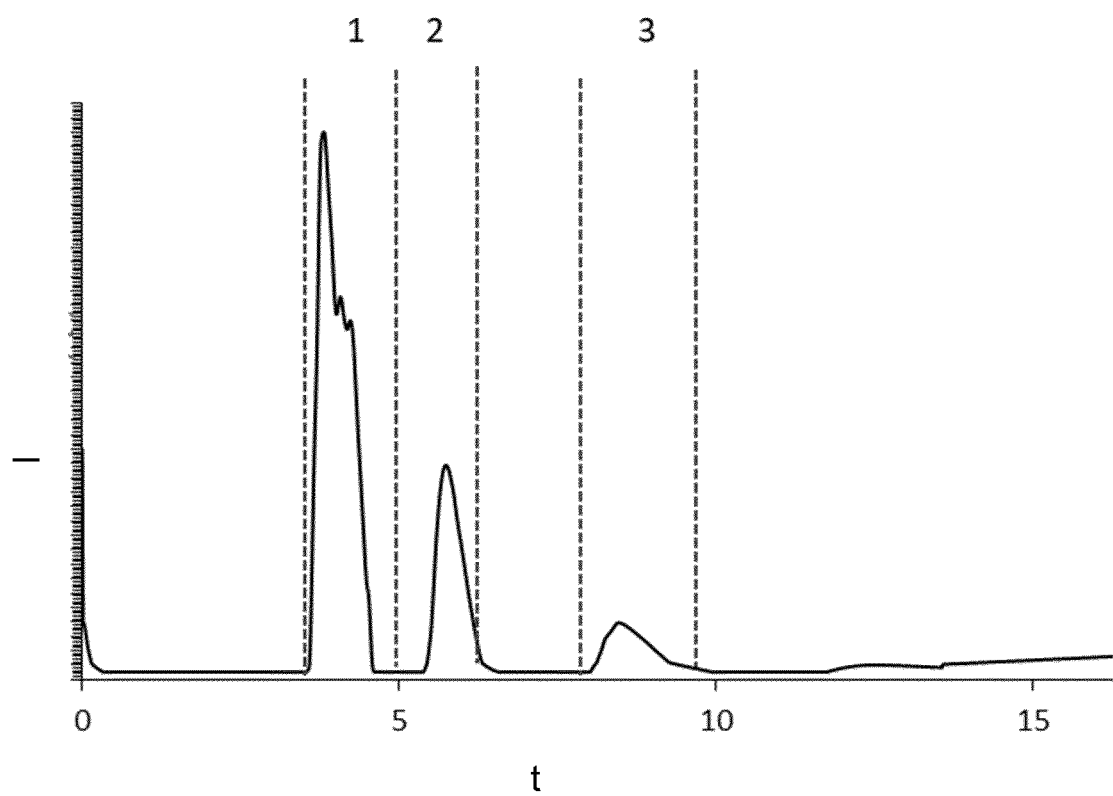
FIG. 8. refers to the three fractions obtained by means of preparative RP-HPLC on a Monochrom column of reaction mixture obtained in section 2.8.1. for the preparation of the mixture comprising an amount from 86 to 99% area/area measured by HPLC-MS of a compound of formula (IJ). Units of scheme are as follows: "I" is intensity in [mAU] and "t" is time in minutes.

Three fractions were separated as shown in FIG. 8.

The mixture comprising an amount from 86% to 99% by weight measured by quantitative proton-NMR of a compound of formula (IJ) of the present invention is the fraction 3 obtained by means of the preparative RP-HPLC on a MonoChrom column as defined above. The compound of formula (IJ) was characterized from fraction 3 by means of UHPLC/TOF/MS (cf. section 1.9.).

3. Sensory Test

3.1. General Procedure for the Sensory Evaluation of the Compounds of Formula (IA), (IB), (IC), (ID), (IE), (IF), (IG), (IH) and (IJ) of the Present Invention This sensory test allowed evaluating the capacity of the compounds of formula (IA), (IB), (IC), (ID), (IE), (IF), (IG), (IH) and (IJ) as defined above to enhance taste; particularly kokumi and/or umami taste. This test allowed measuring the taste threshold of the mixtures comprising an amount from 86% to 99% by weight measured by quantitative proton-NMR of a compound of formula (IA), (IB), (IC), (ID), (IE), (IF), (IG), (IH) and (IJ) in model broth. The "taste threshold" refers to the minimum taste stimulus needed to detect the presence of a compound of formula (IA), (IB), (IC), (ID), (IE), (IF), (IG), (IH) and (IJ) of the present invention. The lower the taste threshold, the greater the capacity as enhancer; particularly greater the capacity as kokumi and/or umami enhancer.

Samples
Diluted samples of the mixtures comprising a compound of formula (IA), (IB), (IC), (ID), (IE), (IF), (IG) and (IJ) in an amount from 86% to 99% by weight measured by quantitative proton-NMR with model broth.
Model broth as constant black.
Diluted samples of comparative samples with model broth:
Comparative compound 1: 5-(aminomethyl)-2-methylpyrimidin-4-amine (Berkshire, United Kingdom)
Comparative compound 2: (4-amino-2-methylpyrimidin-5-yl)methanol (Carbosynth-Berkshire, United Kingdom)
Comparative compound 3: Thiamine (Sigma-Aldrich, Steinheim, Germany)

Preparation of the Samples
Model broth: The model broth comprises the following composition: 1.9 g/L of sodium Sodium chloride (Sigma Aldrich, Steinheim, Germany); 1.9 g/L of mono sodium L-glutatmate (Merck, Darmastadt, Germany); 6.4 g/L of Maltodextrin (Sigma Aldrich, Steinheim, Germany); and 2.1 g/L yeast extract (Gistex GSX II, DSM Food specialities Savoury Ingredients; Delft, Netherlands). The model broth is prepared by mixing the ingrediets under agitation in an ultrasonic bath.

Diluted samples of the mixtures comprising a compound of formula (IA), (IB), (IC), (ID), (IE), (IF), (IG), (IH) and (IJ) in an amount from 86% to 99% by weight measured by quantitative proton-NMR of the present invention: The pH value of each individual mixture comprising an amount from 86% to 99% by weight measured by quantitative proton-NMR of a compound of formula (IA), (IB), (IC), (ID), (IE), (IF), (IG), (IH) and (IJ) was adjusted to 5.4 by the addition of the appropriate amount of formic acid. Each individual pH adjusted mixture thus obtained was diluted 1:2 successively with the model broth to obtain diluted solutions of the mixture comprising a compound of formula formula (IA), (IB), (IC), (ID), (IE), (IF), (IG), (IH) and (IJ) in a concentration from 10 µmol/L to 1000 µmol/L measured by quantitative proton-NMR.

Diluted samples of the comparative compounds 1-3. A mixture of each individual comparative compound 1-3 with model broth was prepared by successively dilution 1:2 of each individual comparative compound with model broth to obtain the diluted comparative solutions having a concentration from 10 µmol/L to 1000 µmol/L measured by quantitative proton-NMR of the comparative compound.

Method
The diluted solutions of the present invention and the comparative solutions falling outside the scope of protection of the present invention obtained above were presented to the panelists with increasing concentrations of the tested solutions by means of the duo-trio-test according to ISO 10399:2017; using the model broth as constant blank. The panelists were asked to mark the differing samples.

The taste threshold is calculated by means of the geometric mean. The geometric mean of the last and the second last concentration was calculated and taken as the individual threshold. The threshold value of the sensory panel was approximated by averaging the threshold values of the individuals in three independent sessions. Values between individuals and separate sessions differed not more than two dilution steps (cf. Lawless, Harry T. "Sensory Evaluation of Food". Springer, $2^{nd}$ edition, 2010, pp. 125-145)

Results
The taste thresholds of the mixture comprising a compound of formula formula (IA), (18), (IC), (ID), (IE), (IF), (IG), (IH) and (IJ) in an amount from 86% to 99% by weight measured by quantitative proton-NMR of the present invention are listed in the table below:

| Mixture comprising an amount from 86% to 99% by weight measured by quantitative proton-NMR of the present invention | savoury taste threshold in model broth [µmol/L] |
|---|---|
| Mixture comprising (IA) | 120 (kokumi) |
| Mixture comprising (IB) | 40 (kokumi) |

-continued

| Mixture comprising an amount from 86% to 99% by weight measured by quantitative proton-NMR of the present invention | savoury taste threshold in model broth [µmol/L] |
|---|---|
| Mixture comprising (IC) | 880 (kokumi) |
| Mixture comprising (ID) | 255 (kokumi) |
| Mixture comprising (IE) | 35 (kokumi) |
| Mixture comprising (IF) | 50 (kokumi) |
| Mixture comprising (IG) | 120 (kokumi) |
| Mixture comprising (IH) | 70 (kokumi) |
| Mixture comprising (IJ) | 80 (kokumi) |

The taste thresholds of the comparative compound 1-3 are listed in the table below:

| Comparative compound | savoury taste threshold in model broth [µmol/L] |
|---|---|
| Comparative compound 1 | >1100 |
| Comparative compound 2 | 700 (kokumi) |
| Comparative compound 3 | 1200 |

The values of the taste thresholds obtained by the compounds of formula of the invention in comparison with the comparative compounds showed that only the compounds formula (IA), (IB), (IC), (ID), (IE), (IF), (IG), (IH) and (IJ) and the corresponding mixtures comprising a compound of formula (IA), (IB), (IC), (ID), (IE), (IF), (IG), (IH) and (IJ) in an amount from 86% to 99% by weight measured by quantitative proton-NMR of the present invention are appropriate for being used as savoury and mouthfulness taste enhancer; particularly as a kokumi and/or umami taste enhancer.

CITATION LIST

1. US2006057268
2. US20170332683
3. US20140127144
4. EP2496097
5. Lawless, Harry T. "Sensory Evaluation of Food". Springer, 2$^{nd}$ edition, 2010, pp. 125-145
6. ISO 10399:2017

For reasons of completeness, various aspects of the invention are set out in the following numbered clauses:

Clause 1. A compound of formula (I')

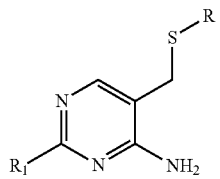

(I')

wherein:
R is a radical selected from the group consisting of

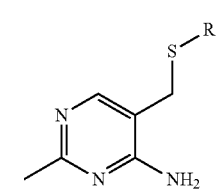

(Rb)

(Rc)

(Rd)

(Re)

; and (Rg)

and $R_1$ is $(C_1$-$C_{12})$alkyl.

Clause 2. The compound of formula (I') according to clause 1, wherein the compound of formula (I') is a compound of formula (I)

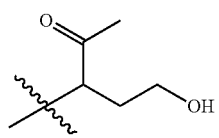

(I)

wherein:
R is a radical selected from the group consisting of

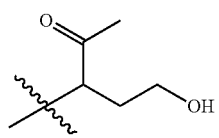

(Rb)

(Rc) 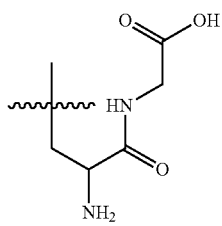

(Rd) 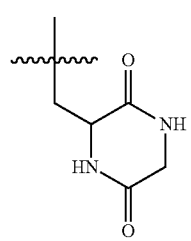

(Re) 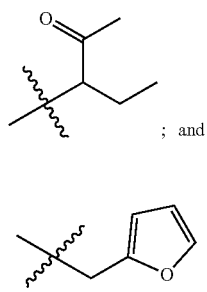

; and (Rg) 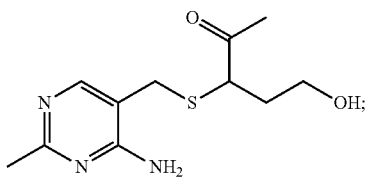

thereby the compound of formula (I) is (IB) 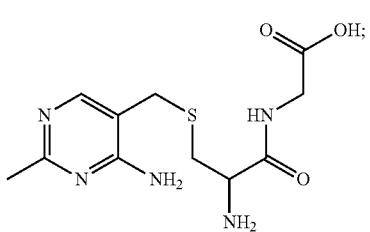

(IC) 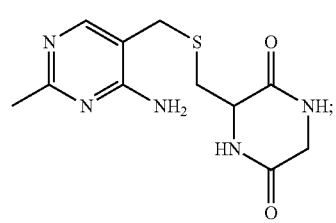

(ID)

(Re) 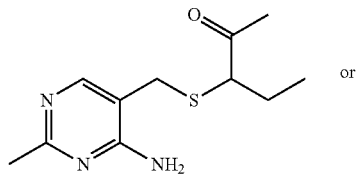

(IG) 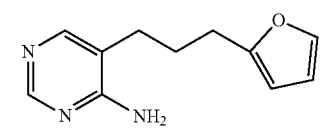

respectively.

Clause 3. A mixture comprising an amount from 86% to 99% by weight measured by quantitative proton-NMR of:
(a) a compound of formula (I) selected from (IB), (IC), (ID), (IE) and (IG) as defined in clause 2; or alternatively
(b) a compound of formula (I) wherein R is (Ra) 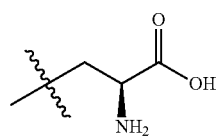

thereby the compound of formula (I) is (IA) 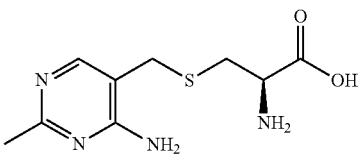

or alternatively
(c) a compound of formula (I) wherein R is (Rf) 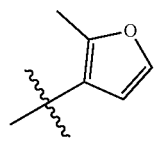

thereby the compound of formula (I) is (IF) 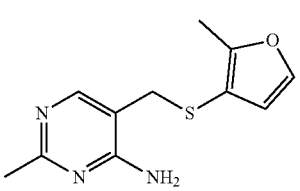

or alternatively
(d) a compound of formula (I) wherein R is CH₃ (Rh) thereby the compound of formula (I) is

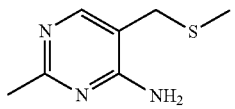
(IH)

or alternatively
(u) a compound of formula (I) wherein R is H (Rj) thereby the compound of formula (I) is

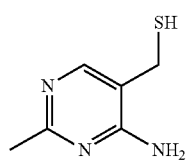
(IJ)

wherein:
when the mixture comprises the compound of formula (IA) or (IB), then the mixture is obtainable by a process which comprises reacting thiamine and L-cysteine followed by a preparative reversed-phase high-performance liquid chromatography purification; and isolating the corresponding fractions;
when the mixture comprises the compound of formula (IC) or (ID), then the mixture is obtainable by a process which comprises reacting thiamine and gluthation followed by a preparative reversed-phase high-performance liquid chromatography purification; and isolating the corresponding fractions;
when the mixture comprises the compound of formula (IE), then the mixture is obtainable by a process which comprises reacting 4-amino-5-(bromomethyl)-2-methylpyrimidin hydrobromide and 3-mercapto-2-pentanone followed by a preparative reversed-phase high-performance liquid chromatography purification;
when the mixture comprises the compound of formula (IF), then the mixture is obtainable by a process which comprises reacting thiamine and 2-methyl-3-furanthiol, followed by a preparative reversed-phase high-performance liquid chromatography purification; and isolating the corresponding fractions;
when the mixture comprises the compound of formula (IG), then the mixture is obtainable by a process which comprises reacting thiamine and 2-furanmethanethiol, followed by a preparative reversed-phase high-performance liquid chromatography purification; and isolating the corresponding fractions;
when the mixture comprises the compound of formula (IH), then the mixture is obtainable by a process which comprises reacting 4-amino-5-(bromomethyl)-2-methylpyrimidin Hydrobromide and sodium thiomethoxide, followed by a preparative reversed-phase high-performance liquid chromatography purification; and isolating the corresponding fractions; and
when the mixture comprises the compound of formula (IJ), then the mixture is obtainable by a process which comprises reacting 4-amino-5-(bromomethyl)-2-methylpyrimidin and sodium thioacetate, adding sodium hydroxide and neutralizing with hydrochloric acid, followed by a preparative reversed-phase high-performance liquid chromatography purification; and isolating the corresponding fractions.

Clause 4. The mixture according to clause 3, wherein when the mixture comprises the compound of formula (IA), then the mixture is obtainable by a process which comprises:
(a) heating a dissolution of a salt of thiamine and L-cysteine at a pH from 3 to 9 at a temperature from 60° C. to 200° C.;
(b) extracting the reaction mixture obtained in step (a) with an organic solvent, to obtain a water fraction and an organic fraction; and
(c) isolating the mixture comprising the compound of formula (IA) from the water fraction obtained in step (b) by means of the preparative reversed-phase high-performance liquid chromatography purification.

Clause 5. The mixture according to clause 3, wherein when the mixture comprises the compound of formula (IB), then the mixture is obtainable by a process which comprises:
(d) heating a dissolution of a salt of thiamine and L-cysteine at a pH of from 3 to 9 at a temperature from 60° C. to 200° C.;
(e) extracting the reaction mixture obtained in step (d) with an organic solvent, to obtain a water fraction and an organic fraction; and
(f) isolating the mixture comprising the compound of formula (IB) from the organic fraction obtained in step (e) by means of the preparative reversed-phase high-performance liquid chromatography purification.

Clause 6. The mixture according to clause 3, wherein when the mixture comprises the compound of formula (IC) or (ID), then the corresponding mixtures are obtainable by a process which comprises:
(g) heating a dissolution of a salt of thiamine and glutathione at a pH of from 3 to 9 at a temperature from 60° C. to 200° C.; and
(h) isolating the corresponding mixtures comprising the compound of formula (IC) or (ID) from the reaction mixture obtained in step (g) by means of the preparative reversed-phase high-performance liquid chromatography purification.

Clause 7. The mixture according to clause 3, wherein when the mixture comprises the compound of formula (IE), then the mixture is obtainable by a process which comprises:
(i) heating a mixture of a compound of formula

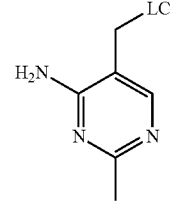

or a salt thereof and 3-mercapto-2-pentanone at a temperature from 0° C. to 60° C.; and
(j) isolating the mixture comprising the compound of formula (IE) from the reaction mixture obtained in step (i) by means of the preparative reversed-phase high-performance liquid chromatography purification, wherein Lg is a leaving group selected from the group consisting of halogen, tosylate and mesylate.

Clause 8. The mixture according to clause 3, wherein when the mixture comprises the compound of formula (IF), then the mixture is obtainable by a process which comprises:

(k) heating a dissolution of a salt of thiamine and 2-Methyl-3-furanthiol at a pH of from 3 to 9 at a temperature from 60° C. to 200° C.; and (l) isolating the corresponding mixtures comprising the compound of formula (IF) from the reaction mixture obtained in step (k) by means of the preparative reversed-phase high-performance liquid chromatography purification.

Clause 9. The mixture according to clause 3, wherein when the mixture comprises the compound of formula (IG), then the mixture is obtainable by a process which comprises:

(m) heating a dissolution of a salt of thiamine and 2-Furanmethanethiol at a pH of from 3 to 9 at a temperature from 60° C. to 200° C.; and (n) isolating the corresponding mixtures comprising the compound of formula (IG) from the reaction mixture obtained in step (m) by means of the preparative reversed-phase high-performance liquid chromatography purification.

Clause 10. The mixture according to clause 3, wherein when the mixture comprises the compound of formula (IH), then the mixture is obtained by a process which comprises:

(p) heating a mixture of a salt of 4-amino-5-(bromomethyl)-2-methylpyrimidin and sodium thiomethoxide at a temperature from 25° C. to 55° C.; and (q) isolating the corresponding mixtures comprising the compound of formula (IH) from the reaction mixture obtained in step (p) by means of the preparative reversed-phase high-performance liquid chromatography purification.

Clause 11. The mixture according to clause 3, wherein when the mixture comprises the compound of formula (IJ), then the mixture is obtained by a process which comprises:

(r) heating a mixture of a salt of 4-amino-5-(bromomethyl)-2-methylpyrimidin and sodium thioacetate at a temperature from 25° C. to 55° C.;

(s) heating the reaction mixture obtained in step (r) at a temperature from 25° C. to 55° C.; (t) adding sodium hydroxide and the resulting mixture is maintained at a temperature from 25° C. to 55° C.; (v) adding hydrochloric acid until neutralization; and (w) isolating the corresponding mixtures comprising the compound of formula (IJ) from the reaction mixture obtained in step (v) by means of the preparative reversed-phase high-performance liquid chromatography purification.

Clause 12. The mixture according to any of the clauses 3-11, wherein the preparative reversed-phase high-performance liquid chromatography purification comprises passing the mixture to be purified through one or more reversed-phase columns under such chromatographic conditions that allows eluting the compound of formula (I) selected from (IA), (IB), (IC), (ID), (IE), (IF), (IG), (IH) and (IJ) and recovering a mixture comprising an amount from 86% to 99% by weight measured by quantitative proton-NMR of the compound of formula (I).

Clause 13. The mixture according to clause 12, wherein when the mixture comprises the compound of formula (IA), then the step (c) is performed by means of a preparative reversed-phase high-performance liquid chromatography sequence comprising:

(c1) firstly, eluting the water fraction obtained in step (b) through a phenyl-Hexyl column using a gradient of 0.1% formic acid in water and acetonitrile;

(c2) secondly, eluting through a Pentafluorphenyl column using a gradient of 0.1% formic acid in water and methanol; and (c3) thirdly, eluting through a TSKgel Amid-80 column using a gradient of 0.1% formic acid in water and acetonitrile; or alternatively wherein when the mixture comprises the compound of formula (IB), then the step (f) is performed by means of a preparative reversed-phase high-performance liquid chromatography sequence comprising:

(f1) firstly, eluting the organic fraction obtained in step (e) through a MonoChrom column using a gradient of 0.1% formic acid in water and acetonitrile; and (f2) secondly, eluting the through a Pentafluorphenyl column using a gradient of 0.1% formic acid in water and methanol; or alternatively wherein when the mixture comprises the compound of formula (IC) or (ID), then the step (h) is performed by eluting the reaction mixture obtained in step (g) through a Phenyl-Hexyl column using a gradient of 0.1% formic acid in water and acetonitrile (step h1); and isolation of the corresponding fractions; or alternatively wherein the mixture comprises the compound of formula (IE), then step (j) is performed by eluting the reaction mixture obtained in step (i) through a Monochrom column using a gradient of 0.1% formic acid in water and acetonitrile (step j1); or alternatively wherein the mixture comprises the compound of formula (IF), then step (l) is performed by means of a preparative reversed-phase high-performance liquid chromatography sequence comprising:

(l1) firstly, eluting the reaction mixture obtained in step (k) through a MonoChrom column using a gradient of 0.1% formic acid in water and acetonitrile; and (l2) secondly, eluting through a Pentafluorphenyl column using a gradient of 0.1% formic acid in water and acetonitrile; or alternatively wherein the mixture comprises the compound of formula (IG), then step (n) is performed by means of a preparative reversed-phase high-performance liquid chromatography sequence comprising:

(n1) firstly, eluting the reaction mixture obtained in step (k) through a MonoChrom column using a gradient of 0.1% formic acid in water and acetonitrile; and (n2) secondly, eluting through a Pentafluorphenyl column using a gradient of 0.1% formic acid in water and acetonitrile; or alternatively wherein the mixture comprises the compound of formula (IH), then step (q) is performed by means of a preparative reversed-phase high-performance liquid chromatography sequence comprising:

(q1) firstly, eluting the reaction mixture obtained in step (p) through a MonoChrom column using a gradient of 0.1% formic acid in water and acetonitrile; and (q2) secondly, eluting through a hydro RP using a gradient of 0.1% formic acid in water and acetonitrile; or alternatively wherein the mixture comprises the compound of formula (IJ), then step (w) is performed by means of a preparative reversed-phase high-performance liquid chromatography sequence comprising:

(w1) eluting the reaction mixture obtained in step (v) through a MonoChrom column using a gradient of 0.1% formic acid in water and acetonitrile.

Clause 14. An edible composition comprising:

one or more of the compounds of formula (IB), (IC), (ID), (IE) or (IG) as defined in any of the clauses 1-2; or alternatively the compounds of formula (IA), (IF), (IH) or (IJ) as defined in clause 3; or alternatively one or more of the mixtures as defined in any of the clauses 3-12; one or more appropriate edible acceptable excipients or carriers; and optionally one or more savoury and mouthfulness imparting flavor compounds.

Clause 15. An edible article comprising:

one or more of the compounds of formula (IB), (IC), (ID), (IE) or (IG) as defined in any of the clauses 1-2; or alternatively the compounds of formula (IA), (IF), (IH) or (IJ) as defined in clause 3; or alternatively one or more of the mixtures as defined in any of the clauses 3-12; or alternatively the edible composition as defined in clause 13; and a foodstuff base comprising one or more savoury and mouthfulness imparting flavor compounds.

Clause 16. Use of a compound of formula (IB), (IC), (ID), (IE) or (IG) as defined in any of the clauses 1-2; or alternatively the compounds of formula (IA), (IF), (IH) or (IJ) as defined in clause 3; or alternatively a mixture as defined in any of the clauses 3-12; or alternatively an edible composition as defined in clause 13 as an savoury and mouthfulness taste enhancer. 73

The invention claimed is:

1. A compound of formula (I')

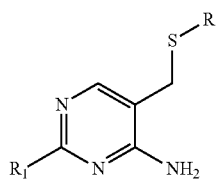
(I')

wherein:

R is a radical selected from the group consisting of

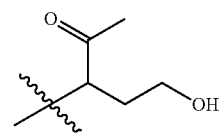
(Rb)

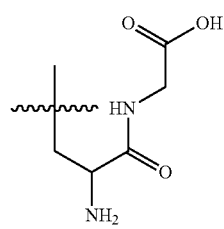
(Rc)

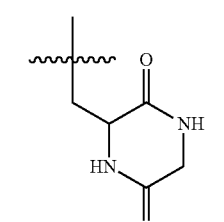
(Rd)

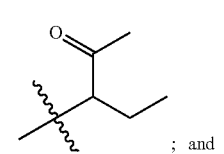
(Re)

; and

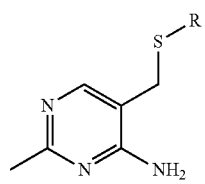
(Rg)

;

and $R_1$ is $(C_1-C_{12})$alkyl.

2. The compound of formula (I') according to claim 1, wherein the compound of formula (I') is a compound of formula (I)

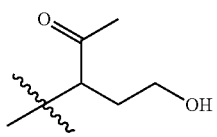
(I)

wherein:

R is a radical selected from the group consisting of

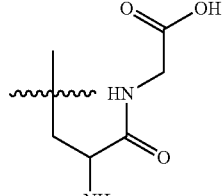
(Rb)

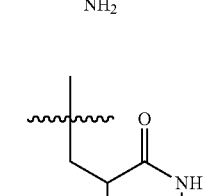
(Rc)

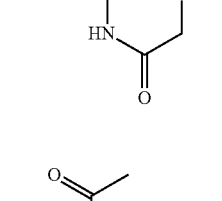
(Rd)

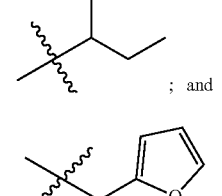
(Re)

; and

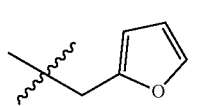
(Rg)

thereby the compound of formula (I) is
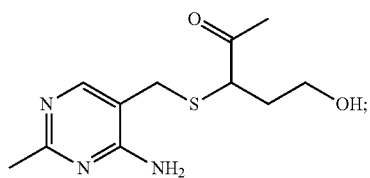
(IB)
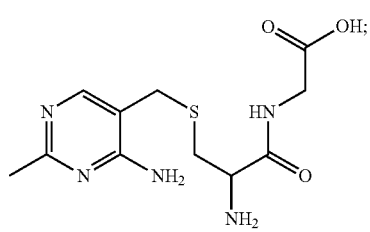
(IC)
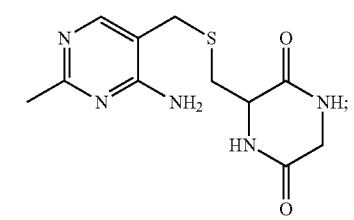
(ID)
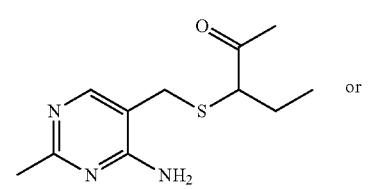
(IE) or
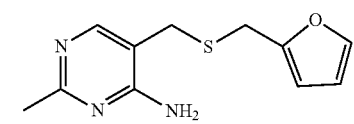
(IG)
respectively.
3. An edible composition comprising:
one or more compounds selected from the group consisting of:
(a) the compounds of formula (I'):
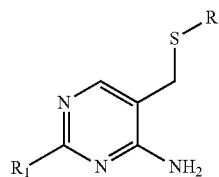
(I')
wherein:
R is a radical selected from the group consisting of
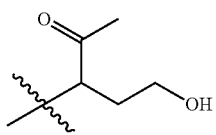
(Rb)
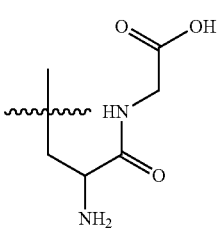
(Rc)
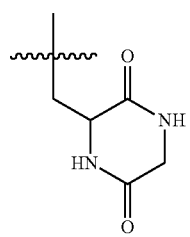
(Rd)
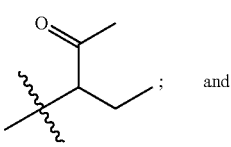
(Re); and
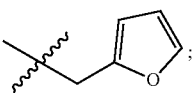
(Rg);
and $R_1$ is $(C_1$-$C_{12})$alkyl;
(b) the compounds of formula (IB), (IC), (ID), (IE), and (IG):
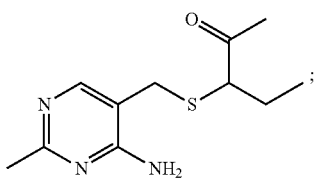
(IB)
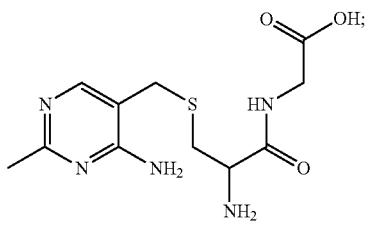
(IC)

-continued

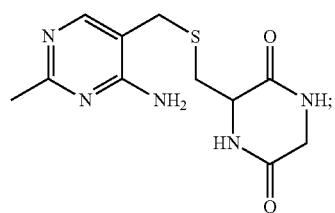
(ID)

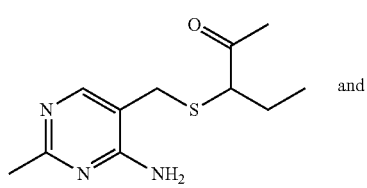
(IE)

and

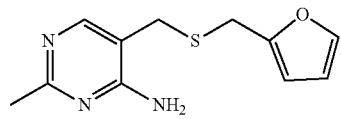
(IG)

respectively; and (c) the compounds selected from the group consisting of (IA), (IF), (IH) and (IJ):

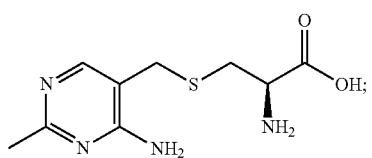
(IA)

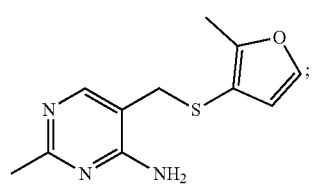
(IF)

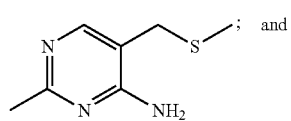
(IH)

and

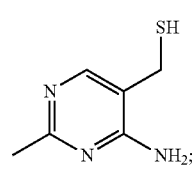
(IJ)

and one or more appropriate edible acceptable excipients or carriers; and optionally one or more flavor compounds.

4. An edible article comprising:
one or more of the compounds selected from the group consisting of:
(a) the compounds of formula (I'):

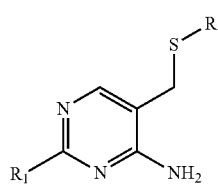
(I')

wherein:
R is a radical selected from the group consisting of

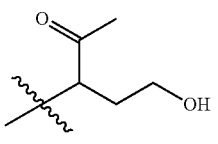
(Rb)

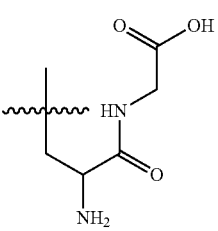
(Rc)

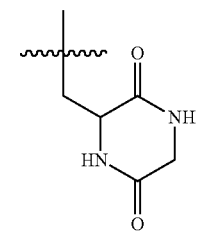
(Rd)

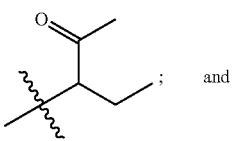
(Re)

and

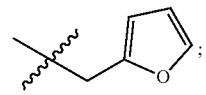
(Rg)

and $R_1$ is $(C_1$-$C_{12})$alkyl;
(b) the compounds selected from the group consisting of formula (IB), (IC), (ID), (IE) and (IG):

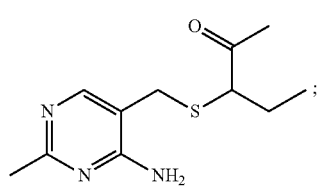
(IB)

-continued

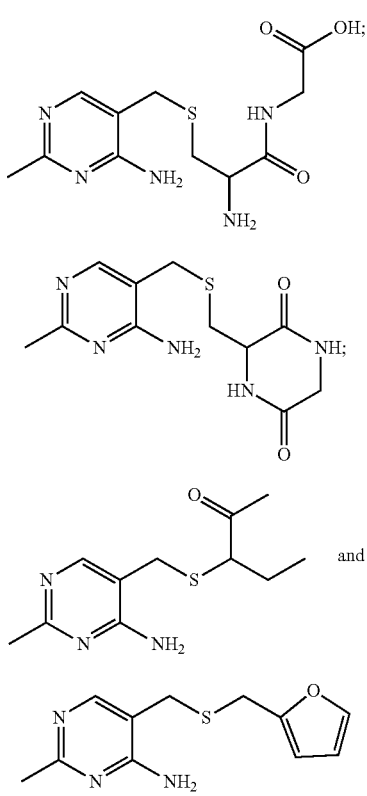

respectively; and
(c) the compounds selected from the group consisting of formula (IA), (IF), and (IJ):

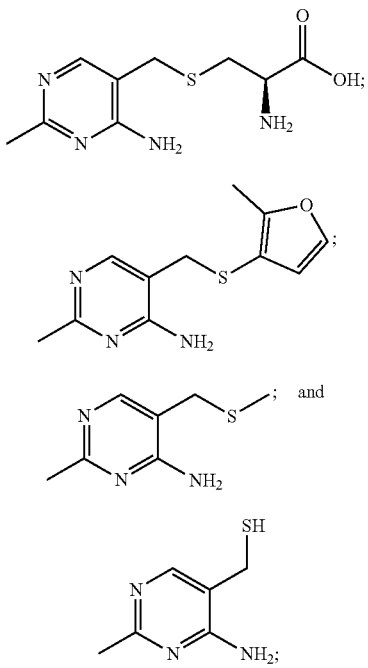

or alternatively the edible composition as defined in claim 3; and a foodstuff base comprising one or more flavor compounds.

5. The edible composition according to claim 3, wherein the one or more flavor compounds are selected from the group consisting of savoury and mouthfulness imparting flavor compounds, sweet imparting flavor compounds, and salty imparting flavor compounds.

6. The edible composition according to claim 3, wherein the one or more flavor compounds are a savoury and mouthfulness imparting flavor compound.

7. The edible composition according to claim 3, wherein the one or more flavor compounds are a savoury and mouthfulness imparting flavor compound selected from umami imparting flavor compounds and kokumi imparting flavor compounds.

8. The edible composition according to claim 3, which is a human food or a non-human animal food.

9. A method of enhancing the taste of food, comprising adding one or more of the compounds selected from the group consisting of:

(a) the compounds of formula (I'):

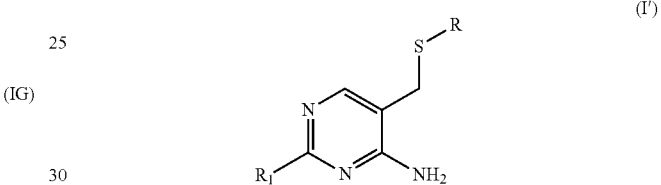

wherein:
R is a radical selected from the group consisting of

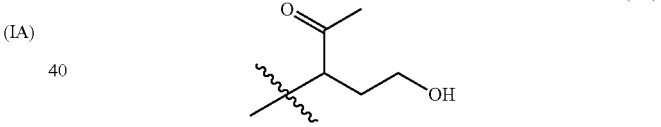

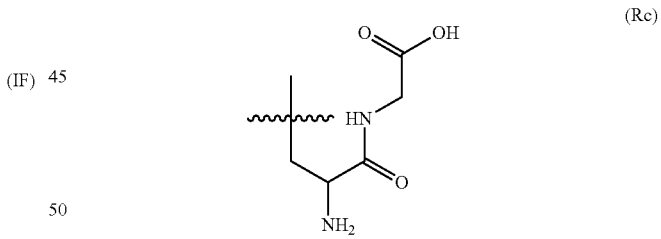

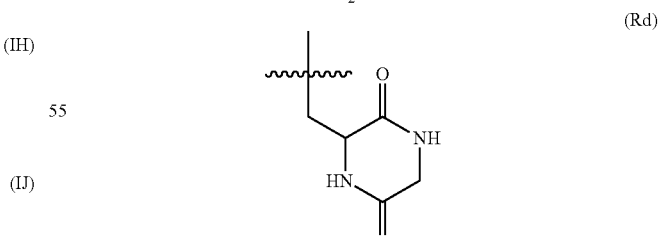

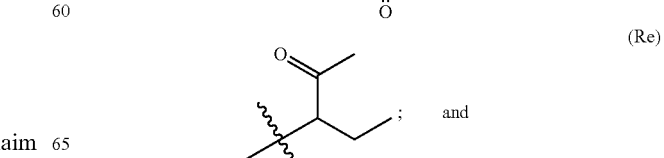

-continued

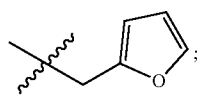
(Rg)

and R₁ is (C₁-C₁₂)alkyl;
(b) the compounds selected from the group consisting of formula (IB), (IC), (ID), (IE) and (IG):

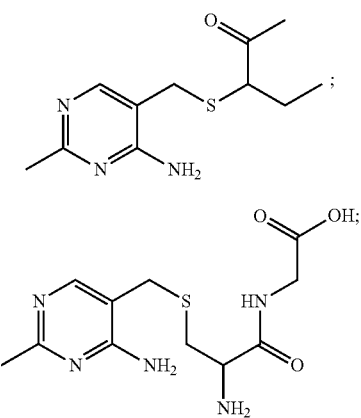
(IB)
(IC)
(ID)

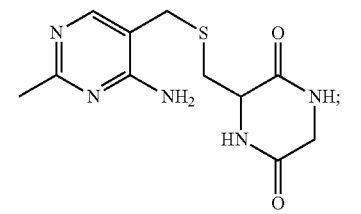
(IE)

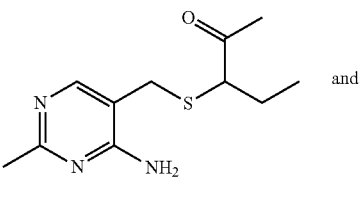
(IG)

respectively; and
(c) the compounds selected from the group consisting of formula (IA), (IF), (IH) and (IJ):

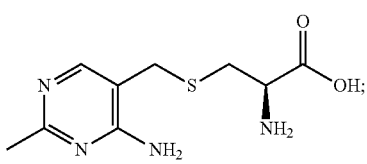
(IA)
(IF)

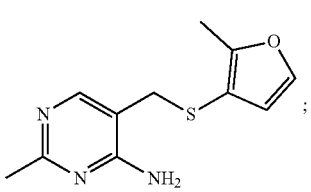
(IH)

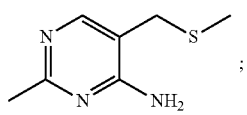
(IJ)

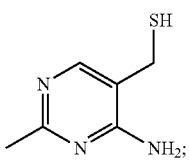

or alternatively adding an edible composition as defined in claim 3, to a foodstuff base.

10. The method of claim 9, wherein the method is for enhancing a savoury and mouthfulness taste, a sweet taste, or a salty taste.

11. The method of claim 9, wherein the method is for enhancing a savoury and mouthfulness taste.

12. The edible article according to claim 4, wherein the flavor compound is selected from the group consisting of savoury and mouthfulness imparting flavor compounds, sweet imparting flavor compounds, and salty imparting flavor compounds.

13. The edible article according to claim 4, wherein the flavor compound is a savoury and mouthfulness imparting flavor compound.

14. The edible article according to claim 4, wherein the flavor compound is a savoury and mouthfulness imparting flavor compounds selected from umami imparting flavor compounds and kokumi imparting flavor compounds.

15. The edible article according to claim 4, which is a human food or a non-human animal food.

\* \* \* \* \*